(12) United States Patent
Meunier et al.

(10) Patent No.: US 7,566,710 B2
(45) Date of Patent: Jul. 28, 2009

(54) DUAL MOLECULES CONTAINING A PEROXIDE DERIVATIVE, SYNTHESIS AND THERAPEUTIC APPLICATIONS THEREOF

(75) Inventors: Bernard Meunier, Castanet (FR); Anne Robert, Toulouse (FR); Odile Dechy-Cabaret, Toulouse (FR); Francoise Benoit-Vical, Palavas les Flots (FR)

(73) Assignee: Centre National de la Racherche Scientifique (C.N.R.S.), Paris (FR)

( * ) Notice: Subject to any disclaimer, the term of this patent is extended or adjusted under 35 U.S.C. 154(b) by 419 days.

(21) Appl. No.: 11/196,979

(22) Filed: Aug. 4, 2005

(65) Prior Publication Data

US 2005/0288315 A1 Dec. 29, 2005

Related U.S. Application Data

(62) Division of application No. 10/240,929, filed as application No. PCT/FR01/01013 on Apr. 4, 2001, now Pat. No. 6,949,569.

(30) Foreign Application Priority Data

Apr. 6, 2000 (FR) .................................. 00 04422

(51) Int. Cl.
C07D 215/38 (2006.01)
A61K 31/4745 (2006.01)
A61K 31/4709 (2006.01)

(52) U.S. Cl. .................. 514/241; 514/269; 514/272; 514/290; 514/300; 514/314; 544/180; 544/310; 546/101; 546/113; 546/159

(58) Field of Classification Search .................. None
See application file for complete search history.

(56) References Cited

FOREIGN PATENT DOCUMENTS

WO WO97/18193 5/1997

OTHER PUBLICATIONS

Basco et al, Antimicrobial Agents and Chemotherapy, vol. 45, No. 6, Jun. 2001, pp. 1886-1888.*

Cabaret, et al. "Preparation and Antimalarial Activities of Trioxiquines. . . ," *Chembiochem*, No. 4, p. 281-283 (2000).

G.E. Bass, et al., "Mechanism of Antimalarial Activity of Chloroquine Analogs," *Journal of Medicinal Chemistry*, vol. 14, No. 4 (1971) p. 275-283, XP002171170.

* cited by examiner

*Primary Examiner*—Zinna N Davis
(74) *Attorney, Agent, or Firm*—Conley Rose, P.C.

(57) ABSTRACT

The invention relates to dual molecules formed from coupling products complying with the formula

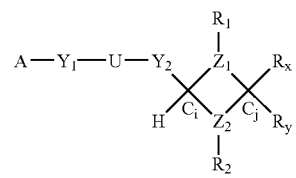

wherein A represents a residue of molecule with anti-malarial activity, $Y_1$ and $Y_2$, represent a linear or branched alkylene chain at C1 to C5, or either $Y_1$ or $Y_2$ is absent, U is an amine, amide, sulphonamide, carboxyl, ether or thioether function, said function linking $Y_1$ and $Y_2$, $Z_1$ and $Z_2$, represent a linear arylene or alkylene, or either $Z_1$ or $Z_2$ is absent, or $Z_1+Z_2$ together represent a cyclic or polycyclic structure including the junction carbons Ci and Cj, $R_1$ and $R_2$, represent a hydrogen atom or a functional group capable of increasing the hydrosolubility of the dual molecule, $R_x$ and $R_y$ form a cyclic peroxide with 4 to 8 chain links, Cj being one of the peaks of said cyclic peroxide, or -$R_x$ or $R_y$ is a cyclic peroxide with 4 to 8 chain links, which may comprise 1 or 2 additional oxygen atoms in the cyclic structure, and one or more substituents $R_3$, identical or different, at least one $R_3$ representing a halogen atom, an —OH group, a —$CF_3$ group, an aryl, an alkyl or alkoxy at C1 to C5, —$NO_2$, the other substituent(s) having one of these correspondences or a hydrogen, and their addition salts with pharmacological acceptable acids.

15 Claims, No Drawings

DUAL MOLECULES CONTAINING A PEROXIDE DERIVATIVE, SYNTHESIS AND THERAPEUTIC APPLICATIONS THEREOF

CROSS-REFERENCE TO RELATED APPLICATIONS

This application is a divisional of U.S. patent application Ser. No. 10/240,929 filed Feb. 4, 2003 (now U.S. Pat. No. 6,949,569), the disclosure of which is hereby incorporated herein by reference. U.S. patent application Ser. No. 10/240,929 is a PCT National Phase application under 35 U.S.C. § 371 of PCT/FR01/01013 filed Apr. 4, 2003, which claims priority of French Patent Application No. 2000/04422 filed Apr. 6, 2000.

The invention relates to dual molecules containing a peroxide derivative, showing particularly an anti-malarial activity, the synthesis and therapeutic applications of said molecules.

Malaria is one of the primary infectious causes of mortality in the world and affects 100 to 200 million people a year. The significant upsurge in the disease observed in recent years is due to several factors, including:

the carriers, i.e. *Anopheles*, which are becoming resistant to conventional inexpensive insecticides such as DDT (abbreviation of trichloro-1,1,1-di(p-chloro-phenyl)-2,2 ethane);

population growth in at-risk zones and, essentially, the resistance of numerous strains of *Plasmodium falciparum*, the parasite responsible for the mortal forms of the disease, to the medicinal products conventionally used, such as chloroquine and mefloquine. The discovery of artemisinine 1, 2, a powerful anti-malarial agent extracted from *Artemisia annua*, drew attention to molecules comprising, like artemisinine, an endoperoxide function 3, 4. Artemisinine and some of its hemi-synthetic derivatives, such as artemether and artesunate, have proved to be very active on resistant *P. falciparum* strains. However, the high cost of these natural compounds and uncertain supply represent major disadvantages. Therefore, the interest of synthetic anti-malarial compounds, which would be accessible at low prices, and offer an action mechanism similar to that of artemisinine, an alkylating effect on the blood and/or parasitic proteins, will be evaluated.

Research on such compounds by the inventors led to the development of a new synthesis strategy based on the use of compounds liable both to be accumulated effectively in the parasite and exert an effect such as that of artemisine.

The inventors observed that forming a covalent bond between a compound with anti-malarial properties and a peroxide type derivative offered coupling products with, surprisingly, a synergic effect between the penetration capacity and activity of the respective constituents on chloroquine-resistant strains and as a general rule a high efficacy for a wide range of parasites.

Therefore, the invention relates to dual molecules presented in the form of coupling products, showing particularly an anti-malarial activity, in particular on *P. falciparum*.

It also relates to a synthesis method for such molecules, comprising a limited number of steps, involving low-cost products, and therefore easy to implement at an industrial scale.

The invention also relates to biological applications of said molecules and particularly the use of their anti-malarial properties to develop medicinal products.

The dual molecules according to the invention are characterised in that they consist of coupling products complying with the formula I

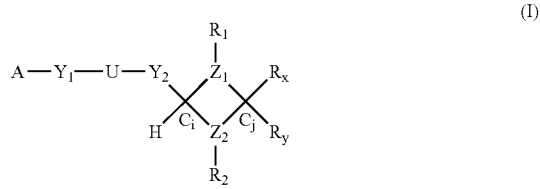

wherein

A represents a residue of molecule with anti-malarial activity, $Y_1$ and $Y_2$, identical or different, represent a linear or ramified alkylene chain at C1 to C5, containing if applicable one or more amine, amide, sulphonamide, carboxyl, hydroxyl, ether or thioether radicals, said alkylene chain at C1 to C5 being substituted if applicable by an alkyl radical at C1 to C5, with the possibility of either $Y_1$ or $Y_2$ being absent, U is an amine, amide, sulphonamide, carboxyl, ether or thioether function, said function linking $Y_1$ and $Y_2$, $Z_1$ and $Z_2$, identical or different, represent a saturated or unsaturated, linear, ramified or cyclic arylene or alkylene radical, with the possibility of either $Z_1$ or $Z_2$ being absent, or $Z_1+Z_2$ together represent a polycyclic structure including the junction carbons Ci and Cj, $R_1$ and $R_2$, identical or different, represent a hydrogen atom or a functional group capable of increasing the hydrosolubility of the dual molecule, advantageously selected from —COOH, —OH, —N($R_a$, $R_b$) where $R_a$ and $R_b$, identical or different, represent a hydrogen atom or an alkyl radical at C1 to C5, $R_x$ and $R_y$ form a cyclic peroxide with 4 to 8 chain links, Cj being one of the peaks of said cyclic peroxide, or $R_x$ or $R_y$ is a cyclic peroxide with 4 to 8 chain links, which may comprise 1 or 2 additional oxygen atoms in the cyclic structure, and one or more substituents $R_3$, identical or different, occupying any separate positions on the cycle, at least one representing a halogen atom, an —OH group, a —$CF_3$ group, an aryl radical, an alkyl or alkoxy radical at C1 to C5, an —$NO_2$ group, the other substituent(s) having one of these correspondences or a hydrogen atom, with the possibility of substituting the carbonated peaks of the cyclic peroxide if applicable by one or more substituents as defined for $R_3$, with the possibility of two adjacent substituents forming a cyclic structure with 5 to 6 chain links, saturated or unsaturated, if applicable substituted by one or more substituents $R_3$ in any position, with the possibility of the other substituent $R_x$ or $R_y$ being $R_3$, and their addition salts with pharmacological acceptable acids.

Advantageously, the residue A drains the coupled compound inside the parasite, which then has an alkylating effect on the blood and/or parasitic proteins.

In a preferred family of derivatives according to the invention, A represents a nitrous heterocycle selected from an aminoquinoline according to formula II or a 1,5-naphtyridine according to formula III below

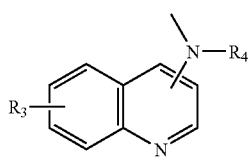 (IIa)

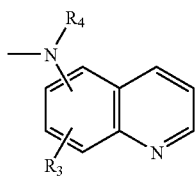 (IIb)

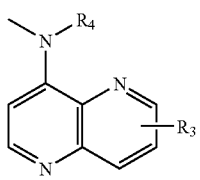 (III)

wherein

R₃ represents one or more identical or different substituents occupying separate position, at least one representing a halogen atom, an —OH group, a —CF₃ group, an aryl radical, an alkyl or alkoxy radical at C1 to C5, an —NO₂ group, the other substituent(s) having one of these correspondences or a hydrogen atom, R₄ represents a linear, ramified or cyclic alkyl radical at C1 to C5, or a hydrogen atom.

In another preferred family according to the invention, A represents a radical according to formula IV $$R_5-CHOH-\qquad (IV)$$

wherein R₅ represents an aryl radical or a nitrous heterocyclic residue.

Preferred correspondences for R₅ consist of 9-phenanthrenyl or 4-quinolinyl radicals, possibly substituted by one or more R₃ groups.

In another preferred family, A represents a phenol-2(aminomethyl) residue according to formula V

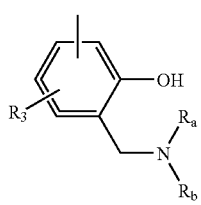 (V)

wherein R₃, Ra and Rb are as defined above.

Another preferred family of dual molecules according to the invention comprises a substituent A representing a biguanide residue selected from proguanil derivatives according to formula VI

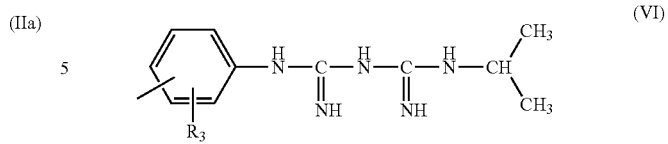 (VI)

or cycloguanil according to formula VII

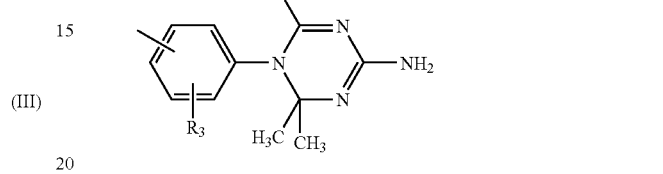 (VII)

wherein R₃ is as defined above.

In another preferred family, A represents a residue of pyrimidine and more particularly of pyrimethamine according to formula VIII

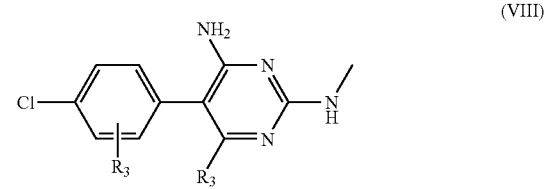 (VIII)

or formula IX

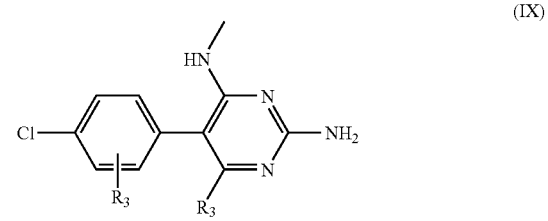 (IX)

wherein R₃ is as defined above.

In another preferred family according to the invention, A represents an acridine residue according to formula X

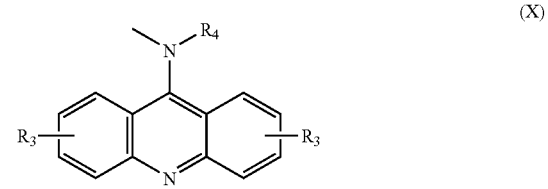 (X)

wherein R₃ and R₄ are as defined above.

The invention relates to dual molecules, such as those defined above, in particular corresponding to the preferred families mentioned above, and wherein $R_x$ and $R_y$ form a cyclic peroxide together.

In more specially preferred dual molecules of this type, $R_x$ and $R_y$ represent a trioxane substituted by one or more substituents $R_3$.

In another preferred embodiment of the invention, used advantageously with the previous embodiment, $Z_1$ and $Z_2$ represent a cyclohexyl or bi-cyclopentyl radical.

In another preferred embodiment, used if required with at least one of the previous embodiments, $Y_1$—U—$Y_2$ are selected so as to modulate the hydrosolubility of the molecule to give it optimal activity.

The invention also relates to a synthesis method for the molecules defined above.

This method comprises the reaction of reactive derivatives of A and peroxide derivatives comprising the residues $R_x$ and $R_y$, so as to form, between these derivatives, a link as defined in relation to formula I.

Various synthesis processes will be easy to access for those skilled in the art using conventional techniques. For example, for peroxide synthesis, it is possible to refer to the work by S. Patai, "The Chemistry of peroxides", John Wiley and Sons Ltd, 1983.

In this way, to prepare dual molecules comprising a trioxane as the peroxide and an aminoquinoline as the derivative A, a compound according to formula XI

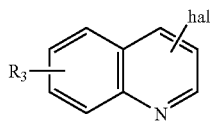

(XI)

wherein $R_3$ is as defined above and "hal" represents a halogen atom, is reacted with a diamine derivative according to formula XII $R_4$—NH—$Y_1$—$U_1$   (XII)

where $R_4$ and $Y_1$ are as defined above and $U_1$ represents an —$NH_2$ group, producing a compound according to formula XIII

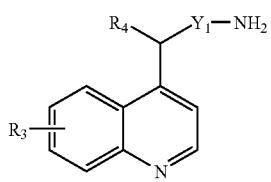

(XIII)

wherein $R_3$, $R_4$ and $Y_1$ are as defined above, b)—irradiation in the presence of molecular oxygen and a photosensitising agent, of a derivative according to formulas XIV to XVII below

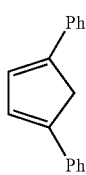

(XIV)

(XV)

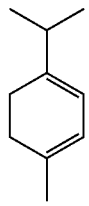

(XVI)

(XVII)

followed by the reaction with a diketone, such as 1,4-cyclohexadione according to formula XVIII or cis-bicyclo(3.3.0)octane-3,7-dione according to formula XIX

(XVIII)

(XIX)

producing trioxanes functionalised with a ketone, according to the general formula XX (XX)

wherein $Z_1$, $Z_2$ and $R_3$ are as defined above, c)—coupling of the derivative according to formula XIII with the trioxane according to formula XX, by reductive amination, followed if applicable by a reaction with a pharmaceutically acceptable acid, to obtain the coupling product in salt form.

Step a is advantageously carried out at a temperature of 80° C. to 140° C. with stirring. The diamine derivative is preferentially used at a rate of 5 molar equivalents. After cooling, the product obtained is recovered by extraction, for example using an organic solvent such as dichloromethane, and then treated if required, for purification purposes.

To carry out step b, photosensitised oxygenation of the initial olefin is performed in the presence of molecular oxygen. The photosensitising agent is advantageously a conventional agent such as tetra-phenylporphyrine or Bengal pink.

The peroxide obtained is then reacted with a diketone, preferentially at a rate of 4 to 10 molar equivalents. The reaction is advantageously carried out in the presence of trimethyl silyl trifluoromethane sulphonate, at a temperature below −50° C., particularly −70° C., for several hours. The functionalised trioxane is then purified. Column chromatography is used for example. A similar protocol is used for the synthesis of trioxane as the precursor of trioxaquines according to formula XIII: 2,3-dimethylbut-2-ene is photo-oxygenated under the above conditions and then placed in the presence of 2 to 10 molar equivalents of an oxoaldehyde, a few drops of trifluoroacetic acid and 2 molar equivalents of N-iodosuccinimide. The reaction is carried out at ambient temperature and protected from light for several hours. The functionalised trioxane is then purified using column chromatography for example.

The coupling step c between the ketone and primary amine is carried out in the presence of a reductive agent such as sodium triacetoborohydride, at ambient temperature.

These compounds are used according to a primary amine/ketone molar ratio of approximately 1.25, the reductive agent being used at a rate of 1.25 equivalents/ketone. To obtain the coupling product in salt form, the basic nitrogens undergo protonation, by adding a pharmacological acceptable acid. For example, citric, tartaric, oxalic and fumaric acid may be used.

The reaction may be carried out with 2 acid equivalents. The protonated product is then recovered and subjected to one or more purification steps if required.

The study of the pharmacological properties of the coupling products according to the invention demonstrated an anti-malarial effect on *P. falciparum* cultured in human red blood cells.

It is particularly important to obtain such an effect as the resistance phenomena of *Plasmodium falciparum* strains, the mortal species, are developing with respect to standard anti-malarial drugs and, in addition, vaccination protection, the subject of considerable research, will not be available for several years.

Therefore, the invention relates to the use of the properties of these coupling products, which also offer the advantage of high safety, to produce pharmaceutical formulations.

The pharmaceutical formulations according to the invention are characterised in that they comprise an effective quantity of at least one coupling product as defined above, associated with a pharmaceutically inert vehicle.

These formulations comprise if required active ingredients of other medicinal products. This may involve an association with any other anti-malarial molecule (amino-quinoline, aryl-alcohol comprising an amine function, amino derivatives of orthocresol, sulphones, sulphonamides, biguanides, amino-pyriminidines, amino-triazines, or quinazolines, and antibiotics (tetracycline, rifampicine, gramicindine D, valinomycine and quinolones in particular) and anti-fungal agents with an anti-malarial activity).

They will also be used advantageously with compounds promoting their assimilation such as sugars like glucose.

The formulations according to the invention are particularly suitable for the treatment of malaria.

Therefore, the invention also relates to the application of the coupling products defined above to the development of medicinal products to treat malaria.

The sales packaging materials, particularly the labelling and package inserts, and advantageously the packaging, are produced according to the planned specific therapeutic application.

The pharmaceutical formulations according to the invention may be administered in different forms, more specifically by the oral, rectal or injectable route.

Formulations administered orally advantageously comprise 40 to 300 mg of active ingredient per dosage unit, preferentially 40 to 100 mg. They advantageously come in the form of tablets, pills, capsules or drops in particular.

The injectable forms comprise 20 to 300 mg of active ingredient per dosage unit, preferentially 50 to 100 mg. They come in the form of solutions for injection by the intravenous, subcutaneous or intramuscular route, produced from sterile or sterilisable solutions. Suspensions or emulsions may also be used.

For rectal administration, suppositories are used.

For example, the dosage that may be used in humans corresponds to the following doses: the patient is administered 50 to 300 mg/day for example, in one or more doses for malaria treatment.

The invention also relates to biological reagents, wherein the active ingredients are composed of the derivatives defined above.

These reagents may be used as references or standards in studies on potential anti-malarial activities.

The invention's other characteristics and advantages will be seen more clearly in the following examples related to the production of quinoline and trioxane coupling products, referred to as "trioxaquines", and the study of their anti-parasitic activity. The formulas of compounds 1 to 34, the synthesis of which is described in these examples are given at the end of the disclosure.

EXAMPLE 1

Trioxaquine 4

Synthesis of
7-chloro-4-[N-(2-aminoethyl)amino]-quinoline 1

A mixture of 4,7-dichloroquinoline (2.0 g, 10 mmol) and 1,2-diaminoethane (2.7 g, 45 mmol) is heated at 85° C. for 5 hours with magnetic stirring. After adding 1N soda (15 ml), the solid obtained is extracted with ethyl acetate (100 ml) at 50° C. The organic phase is washed with distilled water and then using a saturated NaCl solution and then again with distilled water and finally is dried on sodium sulphate. The solvent is evaporated and the product obtained is vacuum-dried (1.3 g, 58%).

NMR $^1$H (250 MHz, CDCl$_3$) δ, ppm: 8.52 (d, $^3J_{HH}$=5.5 Hz, 1H, H2'), 7.94 (d, $^4J_{HH}$=2.2 Hz, 1H, H8'), 7.72 (d, $^3J_{HH}$=8.9 Hz, 1H, H5'), 7.35 (dd, $^3J_{HH}$=8.9 Hz, $^4J_{HH}$=2.2 Hz, 1H, H6'), 6.40 (d, $^3J_{HH}$=5.5 Hz, 1H, H3'), 5.76 (s large, 1H, HN9'), 3.32 (m, 2H, H$_2$C10'), 3.11 (tr, 2H, H$_2$C11'), 1.39 (s large, H$_2$N$_{12}$'). MS (DCI/NH3+) m/z (%): 221 (2), 222 (MH$^+$, 100), 223 (14), 224 (33), 225 (4).

Synthesis of Trioxane Functionalised with a Ketone 2

A mixture of 1,4-diphenyl-1,3-cyclopentadiene (50 mg, 0.23 mmol) and tetraphenylporphyrine (5 mg) in dichloromethane (5 ml) is irradiated in the presence of molecular oxygen (1.15 bar) for 1 hour, at 5° C., with a white bulb (200 W). The peroxide is obtained with a quantitative yield. The unprocessed peroxide in solution in dichloromethane is placed in a bath at −70° C.; 10 molar equivalents of 1,4-cyclohexadione (260 mg, 2.3 mmol) and 0.5 equivalent of trimethylsilyl trifluoromethane sulphonate (20 μl, 0.11 mmol) are added and the reaction mixture is kept under stirring at −70° C. for 4 hours. The reaction is stopped by adding triethylamine (40 μl). After returning to ambient temperature, the reaction medium is washed with distilled water, dried on magnesium sulphate and evaporated to dryness. The functionalised trioxane 2 is purified by chromatography on silica column (hexane/ethyl acetate eluent, 80/20, v/v) (yield: 55%).

NMR $^1$H (250 MHz, CDCl$_3$) δ, ppm: 7.60-7.30 (m, 10H, H-phenyl), 6.35 (d, J$_{HH}$=1.6 and 4.0 Hz, 1H, H6), 5.26 (s large, 1H, H5), 3.31 and 3.05 (2×d, $^2$J$_{HH}$=17.0 Hz, 2×1H, H$_2$C6), 2.56-2.43 (m, 5H), 2.26 (m, 1H), 2.05 (m, 2H).

MS (DCI/NH3+) m/z (%): 363 (MH$^+$, 24), 364 (7), 380 (MNH$_4^+$, 100), 381 (27), 382 (7).

Coupling of Primary Amine with the Ketone by Reductive Amination: Production of Trioxaquine 3

The ketone 2 (99 mg, 0.27 mmol) and the primary amine 1 (76 mg, 0.34 mmol) are placed in solution in CH$_2$Cl$_2$ (5 ml). Sodium triacetoxyborohydride (72 mg, 0.34 mmol) is added. The mixture is kept under stirring at ambient temperature for 18 hours. The reaction medium is then washed with distilled water; the organic phase is dried and the solvent is evaporated to dryness (yield: 87%).

NMR $^1$H (250 MHz, CDCl$_3$) δ, ppm: 8.50 (2×d, 1H, H2'), 7.95 (2×d, 1H, H8'), 7.70 (2×d, 1H, H5'), 7.63-7.25 (m, 11H, H6' and 10H phenyl), 6.35 (m, 2H, H3' and H6), 5.99 (s large, 1H, HN9'), 5.17 (2×s large, 1H, H5), 3.31 (m, 3H, H$_2$C10' and HC8), 3.05 (m, 3H, H$_2$C11' and HC8), 2.61 (m, 2H, cyclohexyl), 2.42 (m, 1H, HC12), 2.10-1.25 (m, 7H, 6H, cyclohexyl and HN12').

MS (DCI/NH3+) m/z (%): 566 (11), 568 (MH$^+$, 100) 569 (38), 570 (41), 571 (12).

Production of Trioxaguine Dicitrate 4

The trioxaquine 3 (25 mg, 0.04 mmol) is placed in solution in acetone (0.5 ml). Citric acid (17 mg, 2.0 equiv.) in solution in acetone (0.5 ml) is added. The trioxaquine dicitrate precipitates; it is centrifuged, washed twice in diethyl ether and vacuum-dried.

NMR $^1$H (250 MHz, CDCl$_3$) δ, ppm: 8.59 (2×d, 1H, H2'), 8.30 (2×d, 1H, H5'), 7.95 (2×d, 1H, H8'), 7.70 (m, 5H, H6' and 4H phenyl), 7.50 (m, 6H, phenyl), 6.73 (2×d, 1H, H3'), 6.60 (2×q, 1H, H6), 5.42 (2×s large, 1H, H5), 3.71 (m, 2H, H$_2$C10'), 3.55-3.25 (m, 4H, H$_2$C11', HC8 and HC12), 3.12 (d, 1H, HC8), 2.76 (d, 4H, citrate), 2.65 (d, 4H, citrate), 2.10-1.50 (m, 8H, cyclohexyl).

MS (ES) m/z (%): in positive mode 568.2 (M$^+$) in negative mode 190.9 (citrate)

Elementary microanalysis: for C$_{46}$H$_{50}$O$_{17}$N$_3$Cl

| | | | |
|---|---|---|---|
| Theor. %: | C 58.01 | H 5.29 | N 4.41 |
| Exper. %: | C 57.65 | H 5.09 | N 4.49 |

EXAMPLE 2

Trioxaguine 7

Synthesis of 7-chloro-4-[N-(3-aminopropyl)amino]-quinoline 5

A mixture of 4,7-dichloroquinoline (5 g, 25 mmol) and 1,3-diaminopropane (9.3 g, 126 mmol) is diamine reflux-heated (118° C.) for 5 hours with magnetic stirring. After cooling, the solid obtained is reflux-extracted with dichloromethane (3×100 ml). The organic phase is washed with distilled water and then dried on sodium sulphate. The concentration of the dichloromethane phase followed by the addition of hexane precipitate the product in the form of a light yellow solid which is filtered, washed with hexane and vacuum-dried (4.5 g, yield=76%).

NMR $^1$H (250 MHz, CDCl$_3$) δ, ppm: 8.48 (d, $^3$J$_{HH}$=5.5 Hz, 1H, H2'), 7.90 (d, $^4$J$_{HH}$=2.2 Hz, 1H, H8'), 7.70 (d, $^3$J$_{HH}$=8.9 Hz, 1H, H5'), 7.50 (s large, 1H, HN9'), 7.29 (dd, $^3$J$_{HH}$=8.9 Hz, $^4$J$_{HH}$=2.2 Hz, 1H, H6'), 6.30 (d, $^3$J$_{HH}$=5.5 Hz, 1H, H3'), 3.39 (m, 2H, H$_2$C10'), 3.03 (tr, 2H, H$_2$C11'), 1.87 (m, 2H, H$_2$C11'), 1.58 (s large, H$_2$N13').

MS (DCI/NH3+) m/z (%): 235 (2), 236 (MH$^+$, 100) 237 (14), 238 (34), 239 (5).

Coupling of Primary Amine with the Ketone by Reductive Amination: Production of Trioxaquine 6

The ketone 2 (199 mg, 0.55 mmol) and the primary amine 5 (165 mg, 0.70 mmol) are placed in solution in CH$_2$Cl$_2$ (10 ml). Sodium triacetoxyborohydride (146 mg, 0.69 mmol) is added. The mixture is kept under stirring at ambient temperature for 15 hours. The reaction medium is then washed with distilled water; the organic phase is dried and the solvent is evaporated to dryness (yield: 96%).

NMR $^1$H (250 MHz, CDCl$_3$) δ, ppm: 8.51 (2×d, 1H, H2'), 8.04 (s large, 1H, HN9'), 7.90 (2×d, 1H, H8'), 7.80 (2×d, 1H, H5'), 7.65-7.25 (m, 11H, H6' and 10H phenyl), 6.30 (m, 2H, H3' and H6), 5.14 (2×s large, 1H, H5), 3.39 (q, 2H, H$_2$C10'), 3.29 (d, 1H, HC8), 2.95 (m, 3H, H$_2$C12' and HC8), 2.60 (m, 2H, cyclohexyl), 2.42 (m, 2H, HC12 and HN13'), 2.10-1.25 (m, 10H, 8H, cyclohexyl and H$_2$C11').

MS (DCI/NH3+) m/z (%): 580 (5), 582 (MH$^+$, 100) 583 (39), 584 (39), 585 (15).

Production of Trioxaquine Dicitrate 7

The trioxaquine 4 (81 mg, 0.14 mmol) is placed in solution in acetone (4 ml). Citric acid (80 mg, 3.0 equiv.) in solution in acetone (5 ml) is added. The trioxaquine dicitrate precipitates; it is centrifuged, washed twice in diethyl ether and vacuum-dried.

NMR $^1$H (250 MHz, DMSO-d$_6$) δ, ppm: 8.60 (2×d, 1H, H2'), 8.42 (2×d, 1H, H5'), 7.93 (2×d, 1H, H8'), 7.65 (m, 5H, H6' and 4H phenyl), 7.45 (m, 6H, phenyl), 6.72 (2×d, 1H, H3'), 6.61 (2×q, 1H, H6), 5.43 (2×s large, 1H, H5), 3.8-3.0 (m, 7H, H$_2$C$_{10}$', H$_2$C12', HC8 and HC12), 2.76 (d, 4H, citrate), 2.65 (d, 4H, citrate), 2.20-1.40 (m, 10H, 8H cyclohexyl and H$_2$c11').

MS (ES) m/z (%): in positive mode 582.3 (M+) in negative mode 190.8 (citrate)

Elementary microanalysis: for C$_{47}$H$_{52}$O$_{17}$N$_3$Cl, 1H$_2$O

| | | | |
|---|---|---|---|
| Theor. %: | C 57.35 | H 5.53 | N 4.27 |
| Exper. %: | C 57.09 | H 5.20 | N 4.24 |

EXAMPLE 3

Trioxaquine 10

Synthesis of 7-chloro-4-[N-(4-aminobutyl)amino]-quinoline 8

A mixture of 4,7-dichloroquinoline (5 g, 25 mmol) and 1,4-diaminobutane (13 ml, 129 mmol) is diamine reflux-heated for 5 hours with magnetic stirring. After cooling, the solid obtained is reflux-extracted with dichloromethane (3×100 ml). The organic phase is washed with distilled water and then dried on sodium sulphate. The concentration of the dichloromethane phase followed by the addition of hexane precipitate the product in the form of a light yellow solid which is filtered, washed with hexane and vacuum-dried (3.4 g, yield=54%).

NMR $^1$H (250 MHz, CDCl$_3$) δ, ppm: 8.50 (d, $^3$J$_{HH}$=5.5 Hz, 1H, H2'), 7.92 (d, $^4$J$_{HH}$=2.2 Hz, 1H, H8'), 7.72 (d, $^3$J$_{HH}$=8.9

Hz, 1H, H5'), 7.31 (dd, $^3J_{HH}$=8.9 Hz, $^4J_{HH}$=2.2 Hz, 1H, H6'), 6.36 (d, $^3J_{HH}$=5.5 Hz, 1H, H3'), 6.04 (s large, 1H, HN9'), 3.29 (m, 2H, H$_2$C10'), 2.81 (tr, 2H, H$_2$C13'), 1.85 (m, 2H, H$_2$C11'), 1.64 (m, 2H, H$_2$C12'), 1.45 (s large, H$_2$N$_{14}$')

MS (DCI/NH3+) m/z (%): 249 (2), 250 (MH$^+$, 100) 251 (18), 252 (36), 253 (5).

Coupling of Primary Amine with the Ketone by Reductive Amination: Production of Trioxaquine 9

The ketone 2 (170 mg, 0.47 mmol) and the primary amine 8 (150 mg, 0.60 mmol) are placed in solution in CH$_2$Cl$_2$ (10 ml). Sodium triacetoxyborohydride (125 mg, 0.59 mmol) is added. The mixture is kept under stirring at ambient temperature for 15 hours. The reaction medium is then washed with distilled water; the organic phase is dried and the solvent is evaporated to dryness (yield: 69%).

NMR $^1$H (250 MHz, CDCl$_3$) δ, ppm: 8.50 (2×d, 1H, H2'), 7.89 (2×d, 1H, H8'), 7.78 (2×d, 1H, H5'), 7.65-7.25 (m, 1H, H6' and 10H phenyl), 6.35 (m, 2H, H3' and H6), 5.96 (s large, 1H, HN9'), 5.18 (2×s large, 1H, H5), 3.30 (m, 3H, H$_2$C10' and HCB), 3.00 (2×d, 1H, HC8), 2.74 (q, 2H, H$_2$C13'), 2.61 (m, 2H, cyclohexyl), 2.46 (m, 1H, HC12), 2.10-1.25 (m, 11H, 6H, cyclohexyl RN14', H$_2$C11'and H$_2$Cl$_2$').

MS (DCI/NH3+) m/z (%): 596 (MH$^+$)

Production of Trioxaquine Dicitrate 10

The trioxaquine 9 (51 mg, 0.09 mmol) is placed in solution in acetone (1 ml). Citric acid (33 mg, 2.0 equiv.) in solution in acetone (1 ml) is added. The trioxaquine dicitrate precipitates; it is centrifuged, washed twice in diethyl ether and vacuum-dried.

NMR $^1$H (250 MHz, DMSO-d$_6$) δ, ppm: 8.56 (2×d, 1H, H2'), 8.45 (2×d, 1H, HS'), 7.95 (m+2×d, 2H, HN9' and H8'), 7.68 (m, 5H, H6' and 4H phenyl), 7.48 (m, 6H, phenyl), 6.72 (2×d, 1H, H3'), 6.60 (2×q, 1H, H6), 5.41 (2×s large, 1H, H5), 3.50 (m, 2H, H$_2$C10'), 3.55-3.10 (m, 5H, H$_2$C13', H$_2$C8' and HC12), 2.75 (d, 4H, citrate), 2.65 (d, 4H, citrate), 2.10-1.50 (12H, 8H cyclohexyl, H$_2$C11' and H$_2$C12').

MS (ES) m/z (%): in positive mode 596.2 (M+) in negative mode 190.8 (citrate)

Elementary microanalysis: for C$_{48}$H$_{54}$O$_{17}$N$_3$Cl, 4H$_2$O

| Theor. %: | C 54.78 | H 5.94 | N 3.99 |
| --- | --- | --- | --- |
| Exper. %: | C 54.88 | H 5.08 | N 4.06 |

EXAMPLE 4

Trioxaquines 13a and 13b

Synthesis of Trioxane Functionalised with a Ketone 11

A mixture of 1,4-diphenyl-1,3-cyclopentadiene (153 mg, 0.7 mmol) and tetraphenylporphyrine (5 mg) in dichloromethane (5 ml) is irradiated in the presence of molecular oxygen (1.15 bar) for 1 hour, at 5° C., with a white bulb (200 W). The peroxide is obtained with a quantitative yield. The unprocessed peroxide in solution in dichloromethane is placed in a bath at −70° C.; 4 molar equivalents of cisbicyclo (3.3.0)octane-3,7-dione (410 mg, 3.0 mmol) and 0.4 equivalent of trimethylsilyl trifluoromethane sulphonate (50 µl, 0.3 mmol) are added and the reaction mixture is kept under stirring at −70° C. for 2 hours. The reaction is stopped by adding triethylamine (100 µl). After returning to ambient temperature, the reaction medium is washed with distilled water, dried on magnesium sulphate and evaporated to dryness.

Chromatography on silica column (hexane/ethyl acetate eluent, 70/30, v/v) is used to separate the two isomer trioxanes 11a and 11b (overall yield: 42%).

Isomer 11a:

NMR $^1$H (250 MHz, CDCl$_3$) δ, ppm: 7.60-7.30 (m, 10H, phenyl), 6.29 (dd, 1H, H6), 5.27 (s large, 1H, H5), 3.21 and 3.02 (2×d, $^2J_{HH}$=17.0 Hz, 2×1H, H$_2$C8), 2.83 (m, 2H), 2.20 (m, 3H), 1.77 (m, 2H).

MS (DCI/NH3+) m/z (%): 406 (MNH$_4^+$, 100), 407 (30), 408 (8).

Isomer 11b:

NMR $^1$H (250 MHz, CDCl$_3$) δ, ppm: 7.60-7.30 (m, 10H, phenyl), 6.32 (dd, 1H, H6), 5.25 (s large, 1H, H5), 3.22 and 3.02 (2×d, $^2J_{HH}$=17.0 Hz, 2×1H, H$_2$C8), 2.90 (m, 2H), 2.50-2.15 (m, 7H), 1.79 (m, 1H).

MS (DCI/NH3+) m/z (%): 404 (3), 405 (3), 406 (MNH$_4^+$, 100), 407 (31), 408 (6), 409 (1).

Coupling of Primary Amine with the Ketone by Reductive Amination: Production of Trioxaquines 12a and 12b The ketone 11a (163 mg, 0.42 mmol) and the primary amine 1 (120 mg, 0.54 mmol) are placed in solution in CH$_2$Cl$_2$ (15 ml). Sodium triacetoxyborohydride (114 mg, 0.54 mmol) is added. The mixture is kept under stirring at ambient temperature for several weeks. The reaction medium is then washed with distilled water; the organic phase is dried and the solvent is evaporated to dryness (yield: 66%).

NMR $^1$H (250 MHz, CDCl$_3$) δ, ppm: 8.42 (d, 1H, H2'), 7.86 (d, 1H, H8'), 7.75 (d, 1H, H5'), 7.65-7.25 (m, 11H, H6' and 10H phenyl), 6.30 (m, 1H, H3'), 6.23 (m, 1H, H6), 6.18 (s large, 1H, HN9'), 5.25 (s large, 1H, H5), 3.57 (s large, 1H, HN12'), 3.37 (m, 3H, H$_2$C10', HC8), 3.20 (m, 2H, HC8 and 1H bicyclopentyl), 3.00 (m, 3H, H$_2$C11' and HC8), 2.75 (m, 1H, bicyclopentyl), 2.45 (m, 2H, HC12 and 1H bicyclopentyl), 2.20 (m, 2H, bicyclopentyl), 1.74-1.10 (m, 5H, bicyclopentyl).

MS (DCI/NH3+) m/z (%): 594 (MH$^+$).

The ketone 11b (148 mg, 0.38 mmol) and the primary amine 1 (110 mg, 0.50 mmol) are placed in solution in CH$_2$Cl$_2$ (15 ml). Sodium triacetoxyborohydride (154 mg, 0.73 mmol) is added. The mixture is kept under stirring at ambient temperature for one week. The reaction medium is then washed with distilled water; the organic phase is dried and the solvent is evaporated to dryness (yield: 68%).

NMR $^1$H (250 MHz, CDCl$_3$) δ, ppm: 8.48 (d, 1H, H2') 7.88 (d, 1H, H8'), 7.73 (d, 1H, H5'), 7.65-7.25 (m, 11H, H6' and 10H phenyl), 6.27 (m, 1H, H3' and H6), 6.06 (s large, 1H, HN9'), 5.25 (s large, 1H, H5), 3.25 (m, 2H, H$_2$C10'), 3.21 (d, 1H, HC8), 3.01 (d, 1H, HC8), 2.94 (m, 3H, H$_2$Cl$_1$' and 3H bicyclopentyl), 2.54 (m, 3H, HC12 and 2H bicyclopentyl), 2.10 (m, 4H, HN12' and 3H bicyclopentyl), 1.77 (m, 1H, bicyclopentyl), 1.25 (m, 3H, bicyclopentyl).

MS (DCI/NH3+) m/z (%): 594 (MH$^+$, 100), 595 (44), 596 (44).

Production of Trioxaquine Dicitrate 13a and 13b

The trioxaquine 12a (166 mg, 0.28 mmol) is placed in solution in acetone (5 ml). Citric acid (160 mg, 3.0 equiv.) in solution in acetone (5 ml) is added. The trioxaquine dicitrate precipitates; it is centrifuged, washed twice in diethyl ether and vacuum-dried.

NMR $^1$H (250 MHz, CDCl$_3$) δ, ppm: 8.63 (d, 1H, H2'), 8.40 (d, 1H, H5'), 8.00 (d, 1H, H8'), 7.70 (m, 5H, H6' and 4H phenyl), 7.50 (m, 6H, phenyl), 6.79 (d, 1H, H3'), 6.60 (q, 1H, H6), 5.53 (s large, 1H, H5), 3.75 (m, 3H, H$_2$C10' and HC8), 3.30 (m, 2H, HC8 and HC12), 3.12 (m, 2H, H$_2$C11'), 2.68 (d, 4H, citrate), 2.39 (m, 4H, citrate), 2.10-1.50 (m, 6H, bicyclopentyl)

MS (ES) m/z (%): in positive mode 594.3 (M$^+$).

Elementary microanalysis: for $C_{48}H_{52}O_{17}N_3Cl$, $1H_2O$

| Theor. %: | C 57.86 | H 5.46 | N 4.22 |
|---|---|---|---|
| Exper. %: | C 58.11 | H 5.02 | N 4.66 |

The trioxaquine 12b (153 mg, 0.26 mmol) is placed in solution in acetone (5 ml). Citric acid (160 mg, 3.0 equiv.) in solution in acetone (5 ml) is added. The trioxaquine dicitrate precipitates; it is centrifuged, washed twice in diethyl ether and vacuum-dried.

NMR $^1$H (250 MHz, DMSO-$d_6$) δ, ppm: 8.60 (d, 1H, H2'), 8.34 (d, 1H, H5'), 7.95 (d, 1H, H8'), 7.73 (m, 5H, H6' and 4H phenyl), 7.51 (m, 6H, phenyl), 6.73 (d, 1H, H3'), 6.60 (q, 1H, H6), 5.55 (s large, 1H, H5), 3.69 (m, 3H, $H_2C10'$ and HC8), 3.44 (m, 1H, HC12), 3.25 (m, 1H, HC8), 3.16 (m, 2H, $H_2C11'$), 2.77 (d, 4H, citrate), 2.65 (m, 4H, citrate), 2.55-2.05 (m, 6H, bicyclopentyl), 1.80-1.40 (m, 4H, bicyclopentyl).

MS (ES) m/z (%): in positive mode 594.3 (M$^+$)
in negative mode 190.9 (citrate)
Elementary microanalysis: for $C_{48}H_{52}O_{17}N_3Cl$, $1H_2O$

| Theor. %: | C 57.86 | H 5.46 | N 4.22 |
|---|---|---|---|
| Exper. %: | C 58.19 | H 5.05 | N 4.17 |

EXAMPLE 5

Trioxaquines 15a and 15b

Coupling of Primary Amine with the Ketone by Reductive Amination: Production of Trioxaquines 14a and 14b The ketone 11a (29 mg, 0.075 mmol) and the primary amine 8 (25 mg, 0.10 mmol) are placed in solution in $CH_2Cl_2$ (5 ml). Sodium triacetoxyborohydride (21 mg, 0.10 mmol) is added. The mixture is kept under stirring at ambient temperature for 48 hours. The reaction medium is then washed with distilled water; the organic phase is dried and the solvent is evaporated to dryness (yield: 64%).

NMR $^1$H (250 MHz, CDCl$_3$) δ, ppm: 8.45 (d, 1H, H2'), 7.92 (d, 1H, H8'), 7.75 (d, 1H, H5'), 7.65-7.25 (m, 11H, H6' and 10H phenyl), 6.33 (m, 2H, H3' and HN9'), 6.27 (m, 1H, H6), 5.25 (s large, 1H, H5), 3.25 (m, 2H, $H_2C10'$), 3.19 (d, 1H, HC8), 3.00 (m, 2H, HC8 and 1H bicyclopentyl), 2.8-2.0 (m, 8H, 4H bicyclopentyl, $H_2C1_1'$, HC12 and HN14'), 1.75-1.10 (m, 5H bicyclopentyl, $H_2C1_1'$ and $H_2Cl_2'$).

MS (DCI/NH3+) m/z (%): 622 (MH$^+$).

The ketone 11b (26 mg, 0.070 mmol) and the primary amine 8 (21 mg, 0.084 mmol) are placed in solution in $CH_2Cl_2$ (15 ml). Sodium triacetoxyborohydride (18 mg, 0.085 mmol) is added. The mixture is kept under stirring at ambient temperature for 48 hours. The reaction medium is then washed with distilled water; the organic phase is dried and the solvent is evaporated to dryness. The mixture obtained contains 70% trioxaquine 12b and is used as is in the next step.

NMR $^1$H (250 MHz, CDCl$_3$) δ, ppm: 8.44 (d, 1H, H2'), 7.90 (d, 1H, H8'), 7.75 (d, 1H, H5'), 7.65-7.25 (m, 11H, H6' and 10H phenyl), 6.30 (m, 3H, H3', H6 and HN9'), 5.24 (s large, 1H, H5), 3.25 (m, 2H, $H_2C10'$), 3.20 (d, 1H, HC8), 3.00 (m, 1H, HC8), 2.85 (m, 1H, bicyclopentyl), 2.65-2.0 (m, 9H, 5H bicyclopentyl, $H_2Cl_3'$, HC12 and HN14'), 1.8-1.6 (m, 5H bicyclopentyl, 1H bicyclopentyl, $H_2Cl_1'$ and $H_2Cl_2'$), 1.24 (m, 3H, bicyclopentyl).

Production of Trioxaquine Dicitrates 15a and 15b

The trioxaquine 14a (30 mg, 0.05 mmol) is placed in solution in acetone (0.4 ml). Citric acid (22 mg, 2.4 equiv.) in solution in acetone (0.4 ml) is added. The trioxaquine dicitrate precipitates; it is centrifuged, washed twice in diethyl ether and vacuum-dried.

NMR $^1$H (250 MHz, DMSO-$d_6$) δ, ppm: 8.59 (d, 1H, H2'), 8.48 (d, 1H, H5'), 8.17 (s large, 1H, HN9'), 7.97 (d, 1H, H8'), 7.70 (m, 5H, H6' and 4H phenyl), 7.50 (m, 6H, phenyl), 6.77 (d, 1H, H3'), 6.57 (q, 1H, H6), 5.50 (s large, 1H, H5), 3.51 (m, 2H, $H_2C10'$ and HC8), 3.10 (m, 4H, $H_2Cl_3'$, HC8 and HC12), 2.78 (d, 4H, citrate), 2.67 (m, 4H, citrate), 2.37 (m, 4H, bicyclopentyl), 2.10-1.50 (m, 10H, 6H bicyclopentyl, $H_2C11'$ and $H_2C12'$).

MS (ES) m/z (%): in positive mode 622.3 (M$^+$)
in negative mode 191.2 (citrate)

The trioxaquine 14b (28 mg, unprocessed mixture) is placed in solution in acetone (1 ml). Citric acid (30 mg, 4.0 equiv.) in solution in acetone (2 ml) is added. The trioxaquine dicitrate precipitates; it is centrifuged, washed twice in diethyl ether and vacuum-dried.

NMR $^1$H (250 MHz, DMSO-$d_6$) δ, ppm: 8.57 (d, 1H, H2'), 8.45 (d, 1H, H5'), 7.93 (d, 1H, H8'), 7.70 (m, 5H, H6' and 4H phenyl), 7.51 (m, 6H, phenyl), 6.70 (d, 1H, H3'), 6.61 (q, 1H, H6), 5.52 (s large, 1H, H5), 4.0-3.0 (m, 7H, $H_2C10'$, $H_2C_{13}'$, $H_2C8$ and HC12), 2.75 (d, 4H, citrate), 2.65 (m, 4H, citrate), 2.55-2.05 (m, 6H, bicyclopentyl), 1.90-1.30 (m, 8H, 4H bicyclopentyl, $H_2C11'$ and $H_2Cl_2'$)

MS (ES) m/z (%): in positive mode 622.4 (M$^+$)
in negative mode 191.2 (citrate)

EXAMPLE 6

Trioxaquine 18

Synthesis of Trioxane Functionalised with a Ketone 16

A mixture of α-terpinene (420 mg, 3.0 mmol) and tetraphenylporphyrine (5 mg) in dichloromethane (5 ml) is irradiated in the presence of molecular oxygen (1.15 bar) for 7 hours, at 5° C., with a white bulb (200 W). The peroxide is obtained with a quantitative yield. The unprocessed peroxide in solution in dichloromethane is placed in a bath at −70° C.; 6 molar equivalents of 1,4-cyclohexadione (2.05 g, 18.3 mmol) and 0.4 equivalent of trimethylsilyl trifluoromethane sulphonate (200 μl, 1.1 mmol) are added and the reaction mixture is kept under stirring at −70° C. for 2 hours. The reaction is stopped by adding triethylamine (400 μl). After returning to ambient temperature, the reaction medium is washed with distilled water, dried on magnesium sulphate and evaporated to dryness. The functionalised trioxane 16 is purified by chromatography on silica column (hexane/ethyl acetate eluent, 85/15, v/v) (yield: 38%).

NMR $^1$H (250 MHz, CDCl$_3$) δ, ppm: 5.40 (m, 1H, H6), 4.00 (m, 1H, HS), 2.67 (m, 1H), 2.41 (m, 4H), 2.22 (m, 4H), 2.00 (m, 3H), 1.50 (m, 1H), 0.99 (m, 9H).

MS (DCI/NH3+) m/z (%): 297 (26), 298 (MNH$_4^+$, 100), 299 (48), 300 (8), 301 (1).

Coupling of Primary Amine with the Ketone by Reductive Amination: Production of Trioxaquine 17

The ketone 16 (113 mg, 0.40 mmol) and the primary amine 1 (115 mg, 0.52 mmol) are placed in solution in $CH_2Cl_2$ (10 ml). Sodium triacetoxyborohydride (109 mg, 0.51 mmol) is added. The mixture is kept under stirring at ambient temperature for 20 hours. The reaction medium is then washed with distilled water; the organic phase is dried and the solvent is evaporated to dryness (yield: 82%).

NMR $^1$H (250 MHz, CDCl$_3$) δ, ppm: 8.50 (2×d, 1H, H2'), 7.92 (2×d, 1H, H8'), 7.69 (2×d, 1H, H5'), 7.35 (2×dd, 1H, H6'), 6.36 (2×d, 1H, H3'), 5.95 (s large, 1H, HN9'), 5.41 (m, 1H, H6), 4.00 (m, 1H, H5), 3.29 (m, 2H, H$_2$C10'), 3.02 (m, 2H, H$_2$C11'), 2.63 (m, 2H), 2.43 (m, 1H), 2.20-1.90 (m, 5H), 1.85 (m, 5H), 1.50 (m, 4H), 1.02 (m, 9H).

MS (DCI/NH3+) m/z (%): 484 (2), 485 (6), 486 (MH$^+$, 100), 487 (36), 488 (42), 489 (12), 490 (2).

Production of Trioxaquine Dicitrate 18

The trioxaquine 17 (45 mg, 0.09 mmol) is placed in solution in acetone (1 ml). Citric acid (53 mg, 3.0 equiv.) in solution in acetone (1 ml) is added. The trioxaquine dicitrate precipitates; it is centrifuged, washed twice in diethyl ether and vacuum-dried.

NMR $^3$H (250 MHz, DMSO-d$_6$) δ, ppm: 8.62 (2×d, 1H, H2'), 8.35 (2×d, 1H, H5'), 7.97 (2×d, 1H, H8'), 7.69 (2×dd, 1H, H6'), 6.75 (2×d, 1H, H3'), 5.45 (m, 1H, H6), 4.17 (m, 1H, H5), 3.75 (m, 2H, H$_2$C10'), 3.35 (m, 2H, H$_2$C11'), 3.05 (m, 1H), 2.76 (d, 4H, citrate), 2.65 (d, 4H, citrate), 2.29 (m, 3H), 2.07 (m, 4H), 1.72 (m, 3H), 1.57 (m, 3H), 1.10 (m, 9H).

MS (ES) m/z (%): in positive mode 486.2 (M$^+$)

| Theor. %: | C 53.84 | H 6.03 | N 4.83 |
|---|---|---|---|
| Exper. %: | C 54.25 | H 5.43 | N 5.04 |

EXAMPLE 7

Trioxaquine 20

Coupling of Primary Amine with the Ketone by Reductive Amination: Production of Trioxaquine 19

The ketone 16 (100 mg, 0.36 mmol) and the primary amine 8 (115 mg, 0.46 mmol) are placed in solution in CH$_2$Cl$_2$ (10 ml). Sodium triacetoxyborohydride (101 mg, 0.48 mmol) is added. The mixture is kept under stirring at ambient temperature for 15 hours. The reaction medium is then washed with distilled water; the organic phase is dried and the solvent is evaporated to dryness (yield: 62%).

NMR $^1$H (250 MHz, CDCl$_3$) δ, ppm: 8.47 (2×d, 1H, H2'), 7.89 (2×d, 1H, H8'), 7.74 (2×d, 1H, H5') 7.35 (2×dd, 1H, H6'), 6.34 (2×d, 1H, H3'), 5.9-5.7 (m, 1H, HN9'), 5.39 (m, 1H, H6), 4.00 (m, 1H, H5), 3.27 (m, 2H, H$_2$C10'), 2.70 (m, 2H, H$_2$Cl$_3$'), 2.60-2.35 (m, 3H), 2.30-1.95 (m, 5H), 1.83 (m, 3H), 1.67 (m, 4H, H$_2$C11' and H$_2$C12'), 1.50 (m, 4H), 1.00 (m, 9H).

MS (DCI/NH3+) m/z (%): 514 (3), 515 (MH$^+$, 100), 516 (28), 517 (36), 518 (11).

Production of Trioxaquine Dicitrate 20

The trioxaquine 19 (46 mg, 0.09 mmol) is placed in solution in acetone (1 ml). Citric acid (44 mg, 2.6 equiv.) in solution in acetone (1 ml) is added. The trioxaquine dicitrate precipitates; it is centrifuged, washed twice in diethyl ether and vacuum-dried.

NMR $^1$H (250 MHz, DMSO-d$_6$) δ, ppm: 8.56 (2×d, 1H, H2'), 8.45 (2×d, 1H, H5'), 7.95 (2×d, 1H, H8'), 7.67 (2×dd, 1H, H6'), 6.72 (2×d, 1H, H3'), 5.45 (m, 1H, H6), 4.15 (m, 1H, H5), 3.50 (m, 2H, H$_2$C10'), 3.20 (m, 1H), 3.05 (m, 2H, H$_2$C13'), 2.76 (d, 4H, citrate), 2.65 (d, 4H, citrate), 2.29 (m, 3H), 2.07 (m, 4H), 1.80 (m, 7H), 1.55 (m, 3H), 1.10 (m, 9H).

MS (ES) m/z (%): in positive mode 514.4 (M$^+$)

Elementary microanalysis: for C$_{41}$H$_{56}$O$_{17}$N$_3$Cl

| Theor. %: | C 54.83 | H 6.29 | N 4.68 |
|---|---|---|---|
| Exper. %: | C 54.32 | H 5.80 | N 4.52 |

EXAMPLE 8

Trioxaquines 23a and 23b

Synthesis of Trioxanes Functionalised with a Ketone 21a, 21b and 21c

A mixture of α-terpinene (320 mg, 2.76 mmol) and tetraphenylporphyrine (5 mg) in dichloromethane (10 ml) is irradiated in the presence of molecular oxygen (1.15 bar) for 7 hours, at 5° C., with a white bulb (200 W). The peroxide is obtained with a quantitative yield. The unprocessed peroxide in solution in dichloromethane is placed in a bath at −70° C.; 4 molar equivalents of cisbicyclo(3.3.0)octane-3,7-dione (1.62 g, 11.7 mmol) and 0.5 equivalent of trimethylsilyl trifluoromethane sulphonate (250 µl, 1.38 mmol) are added and the reaction mixture is kept under stirring at −70° C. for 4 hours. The reaction is stopped by adding triethylamine (400 µl). After returning to ambient temperature, the reaction medium is washed with distilled water, dried on magnesium sulphate and evaporated to dryness. Chromatography on silica column (hexane/ethyl acetate eluent, 70/30, v/v) is used to separate three isomer trioxanes 21a, 21b and 21c, in order of elution (overall yield: 35%).

Isomer 21a:

NMR $^1$H (250 MHz, CDCl$_3$) δ, ppm: 5.37 (d large, 1H, H6), 3.85 (d large, 1H, H5), 3.10-2.60 (m, 3H), 2.48 (m, 2H), 2.16 (m, 6H), 1.90-1.40 (m, 4H), 0.99 (m, 9H).

MS (DCI/NH3+) m/z (%): 323 (4), 324 (MNH$_4^+$, 100), 325 (21), 326 (5).

Isomer 21b:

NMR $^1$H (250 MHz, CDCl$_3$) δ, ppm: 5.38 (d large, 1H, H6), 3.88 (d large, 1H, H5), 2.82 (m, 2H), 2.62 (m, 1H), 2.5-2.0 (m, 10H), 1.72 (m, 1H), 1.49 (m, 1H), 0.99 (m, 9H).

MS (DCI/NH3+) m/z (%): 323 (14), 324 (MNH$_4^+$, 100), 325 (23), 326 (5), 327 (1).

Isomer 21c:

NMR $^1$H (250 MHz, CDCl$_3$) δ, ppm: 5.23 (m, 1H, H6), 4.40 (m, 1H, H5), 3.10-2.6 (m, 3H), 2.49 (m, 2H), 2.17 (m, 6H), 1.9-1.5 (m, 4H), 1.37 (s, 3H), 1.00 (m, 6H).

MS (DCI/NH3+) m/z (%): 323 (26), 324 (MNH$_4^+$, 100), 325 (19), 326 (5), 327 (1).

Coupling of Primary Amine with the Ketone by Reductive Amination: Production of Trioxaquines 22a and 22b The ketone 21a (70 mg, 0.23 mmol) and the primary amine 1 (66 mg, 0.30 mmol) are placed in solution in CH$_2$Cl$_2$ (5 ml). Sodium triacetoxyborohydride (61 mg, 0.29 mmol) is added. The mixture is kept under stirring at ambient temperature for one week. The reaction medium is then washed with distilled water; the organic phase is dried and the solvent is evaporated to dryness (yield: 70%).

NMR $^1$H (250 MHz, CDCl$_3$) δ, ppm: 8.45 (d, 1H, H2'), 7.85 (d, 1H, H8'), 7.70 (d, 1H, H5'), 7.29 (dd, 1H, H6'), 6.31 (d, 1H, H3'), 6.09 (s large, 1H, HN9'), 5.36 (d large, 1H, H6), 3.87 (d large, 1H, H5), 3.31 (m, 2H, H$_2$C10'), 3.11 (m, 2H), 2.99 (m, 2H, H$_2$C11'), 2.75-2.35 (m, 3H), 2.20 (m, 6H), 1.90-1.40 (m, 4H), 1.21 (m, 2H), 0.98 (m, 9H).

MS (DCI/NH3+) m/z (%): 512 (MH$^+$, 100), 513 (32), 514 (46), 515 (15), 516 (7).

The ketone 21b (35 mg, 0.11 mmol) and the primary amine 1 (32 mg, 0.14 mmol) are placed in solution in $CH_2Cl_2$ (5 ml). Sodium triacetoxyborohydride (30 mg, 0.14 mmol) is added. The mixture is kept under stirring at ambient temperature for several weeks. The reaction medium is then washed with distilled water; the organic phase is dried and the solvent is evaporated to dryness (yield: 75%).

NMR $^1$H (250 MHz, CDCl$_3$) δ, ppm: 8.46 (d, 1H, H2t), 7.90 (d, 1H, H8'), 7.76 (d, 1H, H5'), 7.35 (dd, 1H, H6'), 6.34 (d, 1H, H3'), 6.03 (s large, 1H, HN9'), 5.42 (d large, 1H, H6), 3.89 (d large, 1H, H5), 3.26 (m, 2H, H$_2$C10'), 2.97 (m, 3H, H$_2$C11' and 1H), 2.7-1.9 (m, 11H), 1.70 (m, 2H), 1.50 (m, 2H), 1.24 (m, 2H), 0.98 (m, 9H)

MS (DCI/NH3+) m/z (%): 510 (10), 512 (MH$^+$, 100) 513 (35), 514 (51), 515 (16), 516 (7).

Production of Trioxaquine Dicitrates 23a and 23b

The trioxaquine 22a (82 mg, 0.16 mmol) is placed in solution in acetone (5 ml). Citric acid (90 mg, 2.9 equiv.) in solution in acetone (5 ml) is added. The trioxaquine dicitrate precipitates; it is centrifuged, washed twice in diethyl ether and vacuum-dried.

NMR $^1$H (250 MHz, DMSO-d$_6$) δ, ppm: 8.62 (d, 1H, H2'), 8.40 (d, 1H, H5'), 7.97 (d, 1H, H8'), 7.69 (dd, 1H, H6'), 6.78 (d, 1H, H3'), 5.49 (d large, 1H, H6), 4.02 (d large, 1H, H5), 3.78 (m, 2H, H$_2$C10'), 3.65 (m, 1H), 3.32 (m, 2H, H$_2$C11'), 2.79 (d, 4H, citrate), 2.68 (d, 4H, citrate), 2.60-1.90 (m, 9H), 1.80 (m, 4H), 1.10 (m, 9H).

MS (ES) m/z (%): in positive mode 512.3 (M$^+$)
in negative mode 190.8 (citrate)
Elementary microanalysis: for $C_{41}H_{54}O_{17}N_3Cl$

| Theor. %: | C 54.95 | H 6.08 | N 4.69 |
| Exper. %: | C 55.07 | H 6.15 | N 4.52 |

The trioxaquine 22b (44 mg, 0.09 mmol) is placed in solution in acetone (4 ml). Citric acid (50 mg, 3.0 equiv.) in solution in acetone (4 ml) is added. The trioxaquine dicitrate precipitates; it is centrifuged, washed twice in diethyl ether and vacuum-dried.

NMR $^1$H (250 MHz, DMSO-d$_6$) δ, ppm: 8.62 (d, 1H, H2'), 8.36 (d, 1H, H5'), 7.96 (d, 1H, H8'), 7.70 (dd, 1H, H6'), 6.75 (d, 1H, H3'), 5.48 (d large, 1H, H6), 4.05 (d large, 1H, H5), 3.73 (m, 2H, H$_2$C10'), 3.45 (m, 1H), 3.29 (m, 2H, H$_2$C11'), 2.80 (d, 4H, citrate), 2.68 (d, 4H, citrate), 2.31 (m, 6H), 2.06 (m, 4H), 1.8-1.4 (m, 5H), 1.10 (m, 9H)

MS (ES) m/z (%): in positive mode 512.5 (M+)
in negative mode 191.2 (citrate)
Elementary microanalysis: for $C_{41}H_{54}O_{17}N_3Cl, 2H_2O$

| Theor. %: | C 52.81 | H 6.27 | N 4.51 |
| Exper. %: | C 52.93 | H 5.49 | N 5.18 |

EXAMPLE 9

Trioxaquines 25a and 25b

Coupling of Primary Amine with the Ketone by Reductive Amination: Production of Trioxaquines 24a and 24b The ketone 21a (70 mg, 0.23 mmol) and the primary amine 8 (71 mg, 0.28 mmol) are placed in solution in $CH_2Cl_2$ (5 ml). Sodium triacetoxyborohydride (61 mg, 0.29 mmol) is added. The mixture is kept under stirring at ambient temperature for one week. The reaction medium is then washed with distilled water; the organic phase is dried and the solvent is evaporated to dryness (yield: 51%).

NMR $^1$H (250 MHz, CDCl$_3$) δ, ppm: 8.49 (d, 1H, H2'), 7.92 (d, 1H, H8'), 7.74 (d, 1H, H5'), 7.32 (m, 1H, H6'), 6.35 (m, 1H, H3'), 6.0-5.8 (m, 1H, HN9'), 5.39 (d large, 1H, H6), 3.88 (d large, 1H, H5), 3.26 (m, 2H, H$_2$C10'), 2.91 (m, 2H), 2.68 (m, 2H, H$_2$C11'), 2.48 (m, 3H), 2.20 (m, 6H), 1.90-1.40 (m, 8H), 1.22 (m, 2H), 0.97 (m, 9H).

MS (DCI/NH3+) m/z (%): 538 (7), 539 (5), 540 (MH$^+$, 100), 541 (37), 542 (70), 543 (21), 544 (13).

The ketone 21b (35 mg, 0.11 mmol) and the primary amine 8 (40 mg, 0.16 mmol) are placed in solution in $CH_2Cl_2$ (5 ml). Sodium triacetoxyborohydride (33 mg, 0.16 mmol) is added. The mixture is kept under stirring at ambient temperature for several weeks. The reaction medium is then washed with distilled water; the organic phase is dried and the solvent is evaporated to dryness (yield: 76%).

NMR $^1$H (250 MHz, CDCl$_3$) δ, ppm: 8.48 (d, 1H, H2'), 7.90 (d, 1H, H8'), 7.75 (d, 1H, H5'), 7.33 (dd, 1H, H6'), 6.33 (d, 1H, H3'), 6.02 (s large, 1H, HN9'), 5.41 (d large, 1H, H6), 3.90 (d large, 1H, H5), 3.25 (m, 2H, H$_2$C10'), 2.93 (m, 1H), 2.67 (m, 2H, H$_2$C11'), 2.45 (m, 3H), 2.20 (m, 6H), 2.00 (m, 2H), 1.8-1.6 (m, 6H), 1.48 (m, 1H), 1.25 (m, 2H), 1.00 (m, 9H).

MS (DCI/NH3+) M/z (%): 538 (10), 539 (9), 540 (MH$^+$, 100), 541 (40), 542 (40), 542 (67), 543 (23), 544 (14).

Production of Trioxaquine Dicitrates 25a and 25b

The trioxaquine 24a (63 mg, 0.12 mmol) is placed in solution in acetone (5 ml). Citric acid (70 mg, 3.0 equiv.) in solution in acetone (5 ml) is added. The trioxaquine dicitrate precipitates; it is centrifuged, washed twice in diethyl ether and vacuum-dried.

NMR $^1$H (250 MHz, DMSO-d$_6$) δ, ppm: 8.58 (d, 1H, H2'), 8.49 (d, 1H, H5'), 8.14 (s large, 1H, HN9'), 7.97 (d, 1H, H8'), 7.70 (dd, 1H, H6'), 6.77 (d, 1H, H3'), 5.48 (d large, 1H, H6), 4.03 (d large, 1H, H5), 3.50 (m, 2H, H$_2$C10'), 3.36 (m, 1H), 3.04 (m, 2H, H$_2$C13'), 2.75 (d, 4H, citrate), 2.65 (d, 4H, citrate), 2.60-1.95 (m, 9H), 1.90-1.45 (m, 10H), 1.10 (m, 9H).

MS (ES) m/z (%): in positive mode 540.3 (M$^+$)
in negative mode 191.2 (citrate)
Elementary microanalysis: for $C_{43}H_5O_{17}N_3Cl$

| Theor. %: | C 55.88 | H 6.33 | N 4.55 |
| Exper. %: | C 55.35 | H 6.27 | N 4.37 |

The trioxaquine 24b (47 mg, 0.09 mmol) is placed in solution in acetone (4 ml). Citric acid (50 mg, 3.0 equiv.) in solution in acetone (4 ml) is added. The trioxaquine dicitrate precipitates; it is centrifuged, washed twice in diethyl ether and vacuum-dried.

NMR $^1$H (250 MHz, DMSO-d$_6$) δ, ppm: 8.58 (d, 1H, H2'), 8.45 (d, 1H, H5'), 8.01 (s large, 1H, HN9'), 7.95 (d, 1H, H8'), 7.69 (dd, 1H, H6'), 6.75 (d, 1H, H3'), 5.47 (d large, 1H, H6), 4.05 (d large, 1H, H5), 3.48 (m, 2H, H$_2$C10'), 3.35 (m, 1H), 3.03 (m, 2H, H$_2$C13'), 2.76 (d, 4H, citrate), 2.65 (d, 4H, citrate), 2.30 (m, 6H), 2.06 (m, 4H), 1.9-1.4 (m, 9H), 1.09 (m, 9H)

MS (ES) m/z (%): in positive mode 540.4 (M$^+$)
in negative mode 191.0 (citrate)

| Theor. %: | C 54.80 | H 6.42 | N 4.46 |
|---|---|---|---|
| Exper. %: | C 54.93 | H 6.01 | N 4.44 |

EXAMPLE 10

Trioxaquines 28a and 28b

Synthesis of Trioxanes Functionalised with a Ketone 26a and 26b

A mixture of 1,3-cyclohexadiene (400 mg, 5 mmol) and tetraphenylporphyrine (5 mg) in dichloromethane (10 ml) is irradiated in the presence of molecular oxygen (1.15 bar) for 1 hour, at 5° C., with a white bulb (200 W). The peroxide is obtained with a quantitative yield. The unprocessed peroxide in solution in dichloromethane is placed in a bath at −70° C.; 4 molar equivalents of 1,4 cyclohexanedione (2.3 g, 20 mmol) and 0.4 equivalent of trimethylsilyl trifluoromethane sulphonate (500 µl, 2.8 mmol) are added and the reaction mixture is kept under stirring at −70° C. for 4 hours. The reaction is stopped by adding triethylamine (1000 µl). After returning to ambient temperature, the reaction medium is washed with distilled water, dried on magnesium sulphate and evaporated to dryness. Chromatography on silica column (hexane/ethyl acetate eluent, 70/30, v/v) is used to separate the two isomer trioxanes 26a and 26b (overall yield: 2%).

Isomer 26a:

NMR $^1$H (250 MHz, CDCl$_3$) δ, ppm: 5.70 (m, 1H, H6), 5.57 (m, 1H, H7), 4.50 (m, 1H, H5), 4.25 (ddd, 1H, H10), 2.68 (m, 1H), 2.45 (m, 5H), 2.32 (m, 2H), 2.03 (m, 2H), 1.90 (m, 1H), 1.55 m, 1H).

MS (DCI/NH3+) m/z (%): 241 (2), 242 (MNH4+, 100) 243 (16), 244 (5).

Isomer 26b:

NMR $^1$H (250 MHz, CDCl$_3$) δ, ppm: 6.00 (m, 1H), 5.73 (m, 1H), 4.50 (m, 1H), 4.20 (m, 1H), 2.60-1.80 (m, 12H).

MS (DCI/NH3+) m/z (%): 241 (2), 242 (MNH$_4$$^+$, 100) 243 (17), 244 (5).

Coupling of Primary Amine with the Ketone by Reductive Amination: Production of Trioxaquines 27a and 27b The ketone 26a (9 mg, 0.04 mmol) and the primary amine 1 (12 mg, 0.05 mmol) are placed in solution in CH$_2$Cl$_2$ (3 ml). Sodium triacetoxyborohydride (21 mg, 0.10 mmol) is added. The mixture is kept under stirring at ambient temperature for 15 hours. The reaction medium is then washed with distilled water; the organic phase is dried and the solvent is evaporated to dryness (yield: 35%).

NMR $^1$H (250 MHz, CDCl$_3$) δ, ppm: 8.49 (d, 1H, H2'), 7.93 (2×d, 1H, H8'), 7.75 (2×d, 1H, H5'), 7.37 (m, 1H, H6'), 6.35 (m, 2H, H3' and HN9'), 5.66 (d large, 1H, H6), 5.55 (d large, 1H, H7), 4.48 (d large, 1H, H5), 4.15 (d large, 1H, H10), 3.38 (m, 2H, H$_2$C10'), 3.10 (m, 2H, H$_2$C11'), 2.67 (m, 2H), 2.49 (m, 3H), 2.30 (m, 2H), 2.10-1.30 (m, 7H).

MS (DCI/NH3+) m/z (%): 430 (MH$^+$, 100), 431 (30), 432 (47).

The ketone 26b (7 mg, 0.03 mmol) and the primary amine 1 (15 mg, 0.07 mmol) are placed in solution in CH$_2$Cl$_2$ (5 ml). Sodium triacetoxyborohydride (12 mg, 0.06 mmol) is added. The mixture is kept under stirring at ambient temperature for one week. The reaction medium is then washed with distilled water; the organic phase is dried and the solvent is evaporated to dryness (yield: 45%).

NMR $^1$H (250 MHz, CDCl$_3$) δ, ppm: 8.50 (2×d, 1H, H2'), 7.92 (2×d, 1H, H8'), 7.70 (2×d, 1H, H5'), 7.36 (2×dd, 1H, H6'), 6.34 (2×d, 1H, H3'), 6.06 (s large, 1H, HN9'), 5.99 (m, 1H, H6), 5.72 (m, 1H, H7), 4.41 (m, 1H), 4.10 (m, 1H), 3.32 (m, 2H, H$_2$C10'), 3.05 (m, 2H, H$_2$C11'), 2.63 (m, 2H), 2.30 (m, 4H), 2.10 (m, 1H), 2.00-1.35 (m, 7H).

MS (DCI/NH3+) m/z (%): 428 (15), 429 (9), 430 (MH$^+$, 100), 431 (30), 432 (49), 433 (14).

Production of Trioxaquine Dicitrate 28b

The trioxaquine 27b (6 mg, 0.014 mmol) is placed in solution in acetone (1 ml). Citric acid (10 mg, 3.7 equiv.) in solution in acetone (1 ml) is added. The trioxaquine dicitrate precipitates; it is centrifuged, washed twice in diethyl ether and vacuum-dried.

NMR $^1$H (250 MHz, DMSO-d$_6$) δ, ppm: 8.65 (d, 1H, H2'), 8.37 (d, 1H, H5'), 7.98 (d, 1H, H8'), 7.69 (dd 1H, H6'), 6.75 (d, 1H, H3'), 6.05 (m, 1H), 5.80 (m, 1H), 4.57 (m, 1H), 4.30 (m, 1H), 3.75 (m, 2H, H$_2$C10'), 3.34 (m, 3H, H$_2$C13' and 1H), 2.80 (d, 4H, citrate), 2.68 (d, 4H, citrate), 2.50-1.50 (m, 12H).

MS (ES) m/z (%): in positive mode 430.2 (M$^+$)
in negative mode 191.2 (citrate)

| Theor. %: | C 51.65 | H 5.45 | N 5.17 |
|---|---|---|---|
| Exper. %: | C 51.69 | H 5.18 | N 4.66 |

EXAMPLE 11

Trioxaquine 32

Synthesis of Oxoaldehyde 4-Oxopentanal 29

To a suspension of pyridinium chlorochromate PCC (6.4 g, 30 mmol) in dichloromethane (25 ml) 3-acetylpropan-1-ol (2.0 g, 20 mmol) is slowly added. The reaction mixture is left under stirring at ambient temperature for 2 hours and is then filtered on a silica gel with ether. The black residue is washed twice with ether and the filtered ether-treated phases are pooled and evaporated. The aldehyde is obtained in the form of dark liquid (80% purity, 84% yield).

NMR $^1$H (250 MHz, CDCl$_3$) δ, ppm: 9.75 (S, 1H), 2.70 (s large, 4H), 2.14 (s, 3H).

Synthesis of Trioxane Functionalised with a Ketone 30

A mixture of 2,3-dimethylbut-2-ene (270 mg, 3.2 mmol) and tetraphenylporphyrine (5 mg) in dichloromethane (5 ml) is irradiated in the presence of molecular oxygen (1.15 bar) for 7 hours, at 5° C., with a white bulb (200 W). The peroxide is obtained with a quantitative yield. The unprocessed peroxide in solution in dichloromethane is placed in a bath at −70° C.; 10 molar equivalents of 4-oxopentanal 29 (2.2 mg, 22 mmol) and a few drops of trifluoroacetic acid CF$_3$COOH are added. The mixture is stirred at ambient temperature for 90 minutes and then 2 equivalents of N-iodosuccinimide (1.35 g, 6 mmol) are added and the mixture is kept under stirring and protected from light for 3 hours, after which the reaction medium is washed with 20% sodium thiosulphate followed by distilled water. After drying on sodium sulphate and evaporation to dryness, the functionalised trioxane 30 is purified by chromatography on alumina column (hexane/ether eluent, 50/50, v/v) (yield: 14%).

NMR $^1$H (250 MHz, CDCl$_3$) δ, ppm: 5.39 (t, 1H, H3), 3.31 (d, $^2J_{HH}$=11 Hz, 1H, HC10), 3.12 (d, $^2J_{HH}$=11 Hz, 1H, HC10), 2.55 (m, 2H, H$_2$C12), 2.15 (s, 3H, H$_3$C14), 1.83 (m, 2H, H$_2$C11), 1.48 (2 s, 6H, H$_3$C8 and H$_3$C7), 1.06 (s, 3H, H$_3$C9).

MS (DCI/NH3+) m/z (%): 359 (22), 360 (MNH$_4^+$, 100), 361 (14), 362 (2).

Coupling of Primary Amine with the Ketone by Reductive Amination: Production of Trioxaquine 31

The ketone 30 (13 mg, 0.04 mmol) and the primary amine 1 (15 mg, 0.07 mmol) are placed in solution in CH$_2$Cl$_2$ (4 ml). Sodium triacetoxyborohydride (11 mg, 0.05 mmol) is added. The mixture is kept under stirring at ambient temperature for 7 days. The reaction medium is then washed with distilled water; the organic phase is dried and the solvent is evaporated to dryness (yield: 59%).

NMR $^1$H (250 MHz, CDCl$_3$) δ, ppm: 8.50 (d, 1H, H2'), 7.95 (d, 1H, H8'), 7.72 (d, 1H, H5', 7.39 (2×dd, 1H, H6'), 6.37 (2×d, 1H, H3'), 6.00 (s large, 1H, HN9'), 5.37 (t, 1H, H3), 3.30 (m, 3H, H$_2$C10' and HC10), 3.11 (d, $^2$J$_{HH}$=11 Hz, 1H, HC10), 3.00 (m, 2H, H$_2$C11'), 2.74 (m, 1H, HC13), 1.8 (s large, 1H, HN12'), 1.65-1.55 (m, 4H, H$_2$Cl$_1$ and H$_2$Cl$_2$), 1.50 (2 s, 6H, H$_3$C8 and H$_3$C7), 1.10 (d, 3H, H$_3$Cl$_4$), 1.05 (s, 3H, H$_3$C9).

MS (DCI/NH3+) m/z (%): 547 (6), 548 (MH$^+$, 100), 549 (29), 550 (37), 551 (9).

Production of Trioxaquine Dicitrate 32

The trioxaquine 31 (40 mg, 0.073 mmol) is placed in solution in acetone (1 ml). Citric acid (52 mg, 3.7 equiv.) in solution in acetone (1 ml) is added. The trioxaquine dicitrate precipitates; it is centrifuged, washed twice in diethyl ether and vacuum-dried.

NMR $^1$H (250 MHz, DMSO-d$_6$) δ, ppm: 8.63 (d, 1H, H2'), 8.37 (d, 1H, H5'), 7.99 (d, 1H, H8'), 7.71 (dd, 1H, H6'), 6.77 (d, 1H, H3'), 5.37 (t, 1H, H3), 3.7 (m, 4H, H$_2$C10', HC10 and HC13), 3.34 (m, 3H, H$_2$C11' and HC10), 2.78 (d, 4H, citrate), 2.67 (d, 4H, citrate), 2.0-1.6 (m, 4H), 1.54-1.35 (m, 6H), 1.22 (m, 6H).

MS (ES) m/z (%): in positive mode 548.2 (M+)

in negative mode 191.2 (citrate)

Elementary microanalysis: for C$_{34}$H$_{47}$O$_{17}$N$_3$Cl

| | | |
|---|---|---|
| Theor. %: | C 43.81 | H 5.08 | N 4.51 |
| Exper. %: | C 44.08 | H 4.69 | N 4.72 |

EXAMPLE 12

Trioxaguine 34

Coupling of Primary Amine with the Ketone by Reductive Amination: Production of Trioxaquine 33 The ketone 30 (23 mg, 0.07 mmol) and the primary amine 8 (27 mg, 0.11 mmol) are placed in solution in CH$_2$Cl$_2$ (5 ml). Sodium triacetoxyborohydride (27 mg, 0.13 mmol) is added. The mixture is kept under stirring at ambient temperature for 10 days. The reaction medium is then washed with distilled water; the organic phase is dried and the solvent is evaporated to dryness (yield: 10%).

NMR $^1$H (250 MHz, CDCl$_3$) δ, ppm: 8.50 (d, 1H, H2'), 7.90 (d, 1H, H8'), 7.75 (d, 1H, H5'), 7.34 (2×dd, 1H, H6'), 6.38 (2×d, 1H, H3'), 6.00-5.70 (s large, 1H, HN9'), 5.35 (t, 1H, H3), 3.30 (m, 3H, H$_2$C10' and HC10), 3.11 (d, $^2$J$_{HH}$=11 Hz, 1H, HC10), 2.71 (m, 2H, H$_2$C13'), 2.51 (m, 1H, HC13), 1.78 (m, 4H), 1.65 (m, 4H), 1.48 (2 s, 6H, H$_3$C8 and H$_3$C7), 1.25 (m, 3H), 1.09 (s, 3H, H$_3$C9)

MS (DCI/NH3+) m/z (%): 576 (MH$^+$).

Production of Trioxaquine Dicitrate 34

The trioxaquine 33 (20 mg, 0.035 mmol) is placed in solution in acetone (1 ml). Citric acid (24 mg, 4.5 equiv.) in solution in acetone (1 ml) is added. The trioxaquine dicitrate precipitates; it is centrifuged, washed twice in diethyl ether and vacuum-dried.

NMR $^1$H (250 MHz, DMSO-d$_6$) δ, ppm: 8.62 (d, 1H, H2'), 8.46 (d, 1H, H5'), 7.96 (m, 2H, H8' and HN9'), 7.70 (m, 1H, H6'), 6.73 (d, 1H, H3'), 5.50 (t, 1H, H3), 4.0-3.0 (m, 7H, H$_2$C10', H$_2$Cl$_3$, H$_2$C10' and HC13), 2.77 (d, 4H, citrate), 2.66 (d, 4H, citrate), 1.9-1.6 (m, 8H), 1.53 (m, 6H), 1.4-1.1 (m, 6H).

MS (ES) m/z (%): in positive mode 576.2 (M+)

EXAMPLE 13

Study of the Anti-Malarial Activity of Trioxaguines on P. falciparum.

The in vitro results obtained on P. falciparum cultured in human red blood cells are given below.

Experimental Section

The P. falciparum strains are cultured continuously according to Trager and Jensen's method 5, with the following modifications 6: the parasites are maintained in human red blood cells (O±), diluted to 1% haematocrit in RPMI 1640 medium supplemented with 25 mM Hepes+30 mM NaHCO$_3$ and complemented with 5% AB+ human serum. The parasite populations are synchronised over a 4 hour period by flotation with a gelatine solution, followed by lysis with 5% D-sorbitol 7,8. The Nigerian strain is considered to be susceptible to chloroquines and the FcM29-Cameroon and FcB1-Columbia strains are chloroquine-resistant (IC$_{50}$ for chloroquine >100 nM) 9,10. The anti-malarial activity tests are performed using Desjardins' radioactive micromethod 11. The tests are performed in triplicate, in 96-well microplates, the readings being at 1% haematocrit and 0.5-1% parasitaemia. For each test, the parasites are incubated with decreasing concentrations of drug for either 32 hours and 72 hours (4 wells contain chloroquine diphosphate as a reference). The first dilution of the drug is performed at 10 mg/ml in dimethylsulphoxide and the following dilutions are made with RPMI 1640. The parasite growth is measured with the incorporation of tritiated hypoxanthine compared to incorporation in the absence of drug (taken to be 100%). 12 and the IC$_{50}$ values are determined graphically by plotting the percentage of inhibition as a function of the drug concentration. The IC$_{50}$ values measured after 32 hours, equivalent to the end of the trophozoite stage, are used to evaluated the influence of the compound on parasite maturation, the IC$_{50}$ values measured after 72 hours, corresponding to 1.5 of the life cycle in red blood cells, indicate a possible effect on erythrocyte reinvasion.

Trioxaquine Structures Tested:

Results

Trioxaquines 9, 3 and 6 and trioxaquine citrate 4 were tested independently on the Nigerian, FcB1 and FcM29 strains; the results obtained were compared to those of chloroquine diphosphate and to those of two trioxaquine fragments: quinoline-amine 1 (n=2) and trioxane-ketone 2.

The results are summarised in the following table:

TABLE

IC$_{50}$ values measured for 9, 3, 6, 4 tested independently on three *Plasmodium falciparum* strains.

|  |  | FcB1-Colombia (CQR)[a] | | FcM29-Cameroon (CQR+)[a] | | Nigerian (CQS)[a] | |
| --- | --- | --- | --- | --- | --- | --- | --- |
|  |  | 32 hrs | 72 hrs | 32 hrs | 72 hrs | 32 hrs | 72 hrs |
| 6 | ng/ml | 40 | 35 | 25 | 10 | 50 | 50 |
| (n = 3) | nM | 69 | 60 | 43 | 17 | 86 | 86 |
| 9 | ng/ml | 16 | 10 | 22 | 20 | 20 | 20 |
| (n = 4) | nM | 27 | 17 | 37 | 34 | 34 | 34 |
| 3 | ng/ml | 15 | 5 | 18 | 10 | 1 | 1 |
| (n = 2) | nM | 26 | 9 | 32 | 18 | 1.8 | 1.8 |
| 4 | ng/ml | 35 | 20 | n.d.[b] | n.d.[b] | 33 | 7 |
| (n = 2), citrate | nM | 37 | 21 |  |  | 35 | 8 |
| Quinoline-amine1 | ng/ml | 35 | 20 | n.d.[b] | n.d.[b] | 33 | 7 |
| Trioxane-ketone 2 | nM | 113 | 36 | n.d.[b] | n.d.[b] | 149 | 45 |
| Chloroquine | ng/ml | 75 | 60 | 100 | 80 | 45 | 10 |
| diphosphate[c] | nM | 145 | 116 | 194 | 155 | 87 | 19 |

[a]CQR = chloroquine resistant strain. CQR+ = highly chloroquine resistant strain, CQS = chloroquine susceptible strain.
[b]Not determined.
[c]Given for comparison purposes.

The IC$_{50}$ values obtained for the compounds 3, 4, 6 and 9 are between 5 and 50 ng/ml, which is equivalent to a concentration of 8 to 86 nM.

All the trioxaquine samples are more active than chloroquine, on both susceptible and resistant strains (except for 6 on the Nigerian susceptible strain). The high efficacy of 9, 3 and 4 on the susceptible and resistant strains, significantly greater than the activity of not only chloroquine, but also of each of the two fragments, quinoline-amine 1 (n=2) and trioxane-ketone 2, indicates a significant synergic effect between the trioxane and chloroquinoline fragments of these compounds.

The citrate form of compound 4 increases its solubility considerably in aqueous media while retaining a high activity. Protonation by other acids than citric acid produces salts offering the same advantages (hydrochloride, sulphate, tartrate).

The low IC$_{50}$ values obtained with trioxaquine 3 on the FcB1, FcM29 strains and on the Nigerian strain (9 nM, 18 nM and 1.8 nM respectively) and with 9 and the citrate 4, indicate that the efficacy of these compounds is retained for a wide spectrum of parasites.

EXAMPLE 14

Preparation of Pharmaceutical Formulations Based on Molecules According to the Invention in the form of scored tablets
active ingredient: 100 mg
excipients: starch, hydrated silica, amylaceous ground sugar, gelatine, magnesium stearate.
in the form of film-coated tablets
active ingredient: 300 mg
excipients: Core: wheat starch, amylaceous ground sugar (sucrose powder supplemented with starch), hydrated silica, gelatine, magnesium stearate. Coating: methylhydroxy propylcellulose, poloxyethyleneglycol 20 000.
in the form of syrups
active ingredient: 25 mg/ml
excipients: citric acid, sucrose, coffee extract, caramel, purified water.
in the form of solutions for injection
active ingredient: 100 mg for one 1 ml ampoule, 200 mg for one 2 ml ampoule, 400 mg for one 4 ml ampoule.
excipients: sodium chloride and water for injections.
in the form of 25% solutions for injection
active ingredient: 500 mg
excipients: lactic acid (solubilising agent), formic acid, water for injections.
Preservative: anhydrous sodium sulphite equivalent to 0.61 mg sulphur anhydride/amp.
in the form of 100 mg/ml oral suspensions:
active ingredient: 20 mg/ml.
excipients: microcrystalline cellulose and sodium carboxymethylcellulose, propylene glycol, sorbitol, anhydrous citric acid, sodium citrate, sodium benzoate, banana-vanilla flavour, dimethylpolysiloxane emulsion, purified water.

EXAMPLE 15

Activity of trioxaquine-citrate 4 on human isolates

Trioxaquine-citrate 4, referred to as DU-1102, was tested on human *Plasmodium falciparum* isolates, some of which were chloroquine- and/or pyrimethamine-resistant. The median inhibitory concentration values, IC50, obtained are 11 to 68 ng/ml, corresponding to a geometric mean of 41 ng/ml, i.e. 43 nM.

The activity of DU-1102 on these isolates is independent of their susceptibility or their resistance to the other anti-malarial agents tested.

There is no correlation between DU-1102 on the one hand and chloroquine or pyrimethamine on the other, which indicates the absence of the probability of cross-resistance between DU-1102 and said anti-malarial agents already used.

These results indicate the satisfactory efficacy of trioxaquines on wild *P. falciparum* strains.

Activity of trioxaquine-citrate DU-1302, represented below:

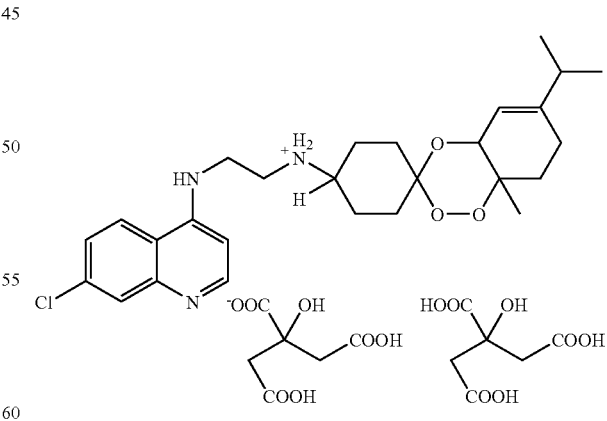

2.1. In vitro, this compound shows an activity, LC50=6 nM on *P. falciparum* in culture.

2.2. The trioxaquine citrate DU-1302 is active in vivo in mice infected with *P. vinckei* ("4 day" test: treatment for 4 consecutive days starting 24 hours after inoculation of the parasite).

ED50=5 mg/kg/day, or 6 μmol/kg/day, by the intraperitoneal route, with no observable re-emergence for 2 months, ED50=18 mg/kg/day, or 20 μmol/kg/day, by the oral route.

2.3. The trioxaquine-citrate DU-1302 does not show any apparent toxicity after administration to healthy mice, at a dose of 100 mg/kg/day by the oral route, for three consecutive days.

3. Absence of mutagenicity of trioxaquine-citrates DU-1102 and DU-1302

The above two compounds do not induce DNA repair (no SOS response in *E. coli* GE864 at concentrations of 5, 10, 15 and 20 μM: the control used is 3 μM mitomycin C). Therefore, they are non-mutagenic for *E. coli* at these concentrations.

Formulas of compounds for which the synthesis is described in the examples

1

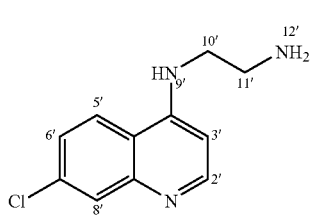

2

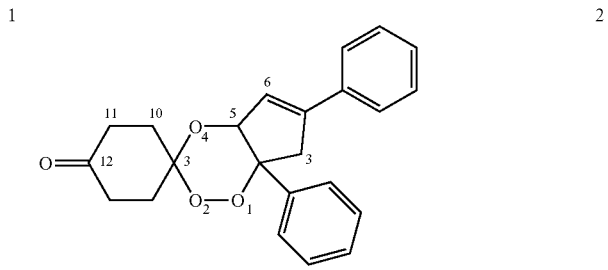

3

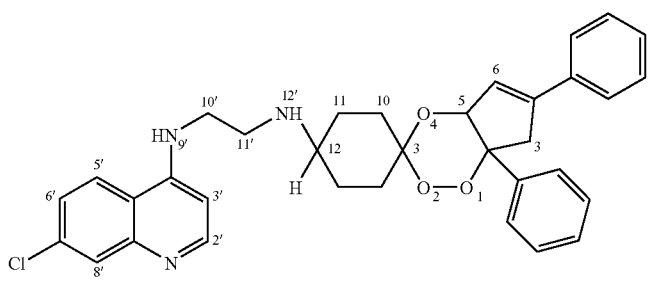

4

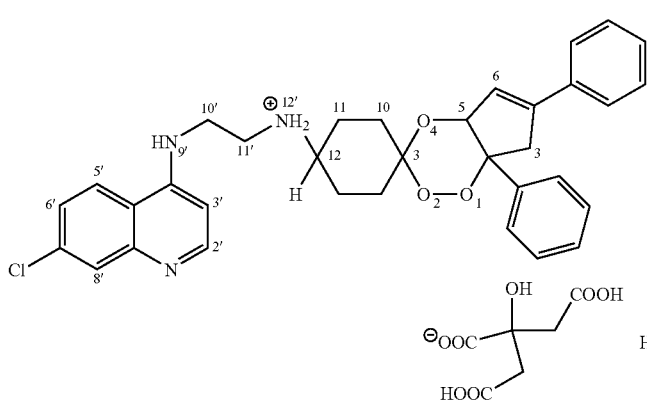

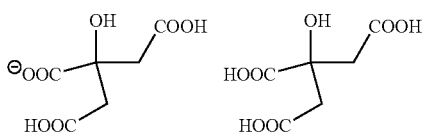

5

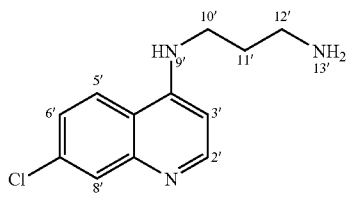

6

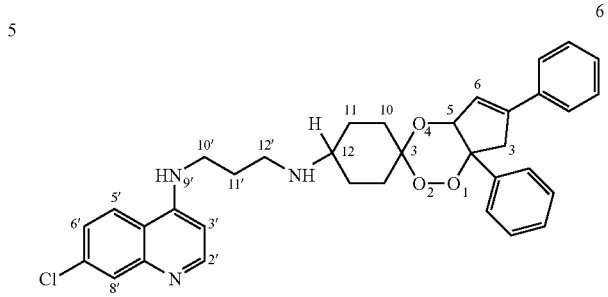

-continued
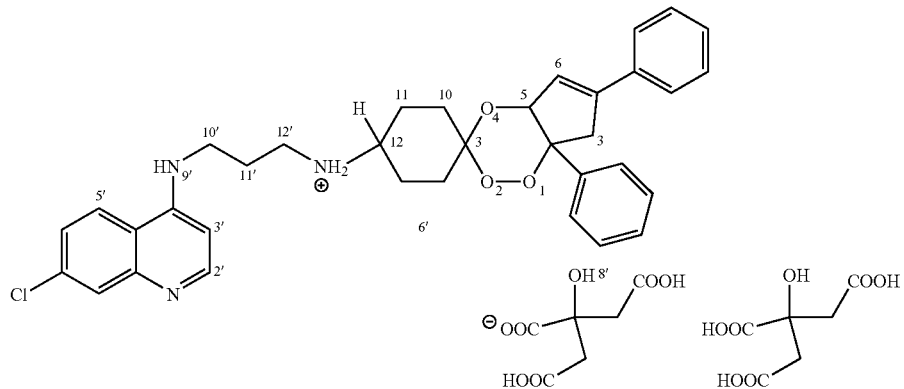
7
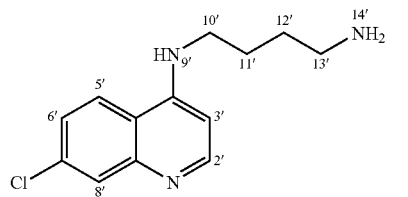
8
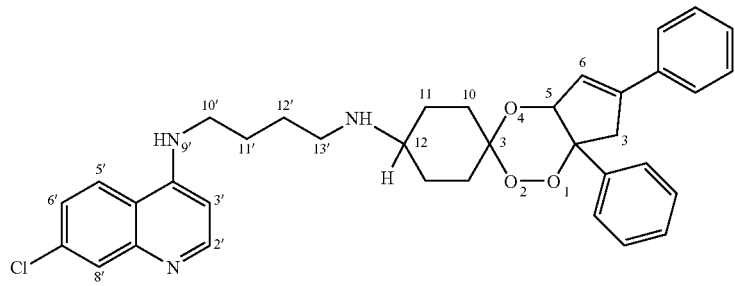
9
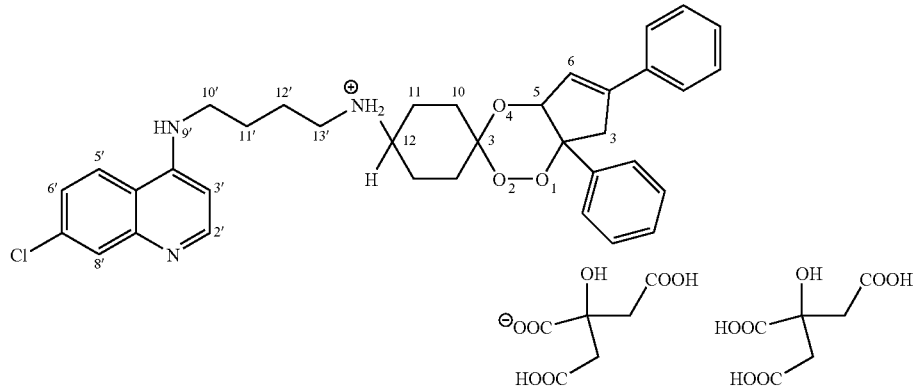
10
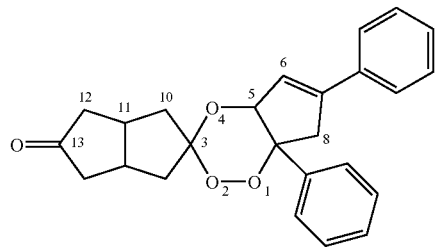
11a et 11b -continued
12a et 12b
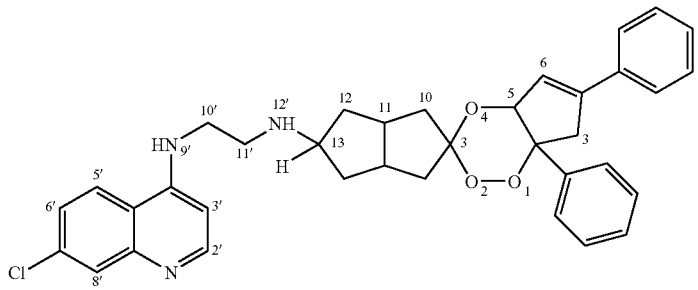
13a et 13b
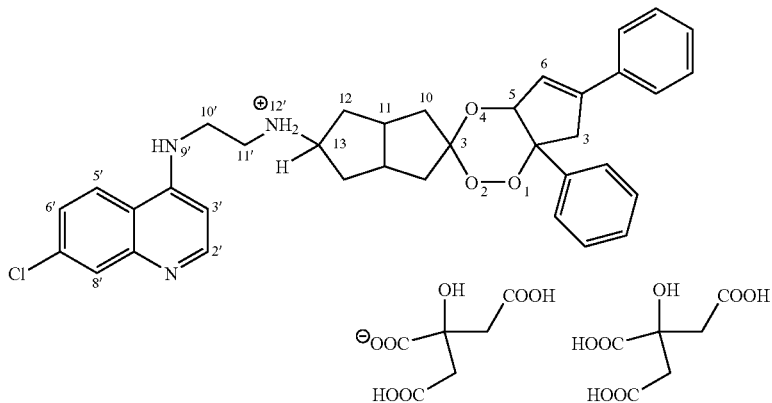
14a et 14b
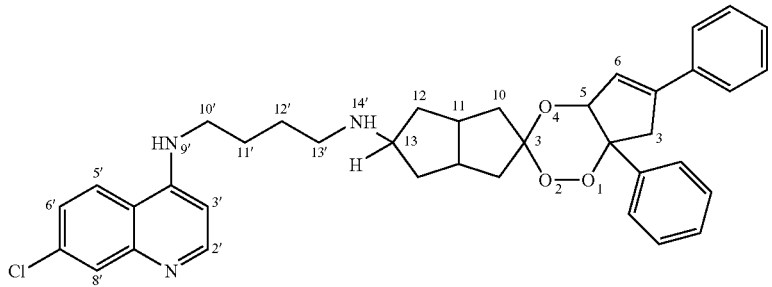
15a et 15b
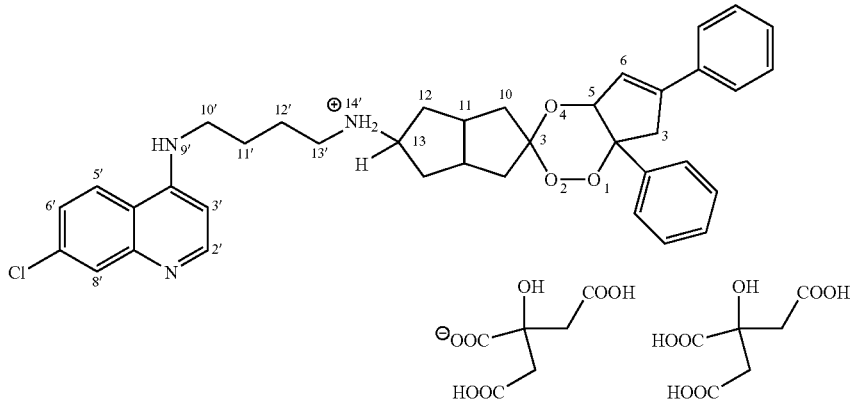

-continued
16
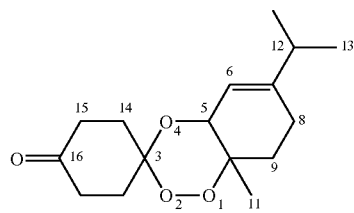
17
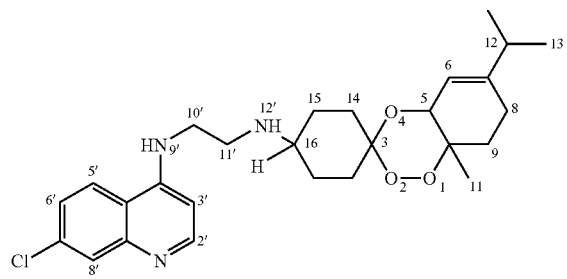
18
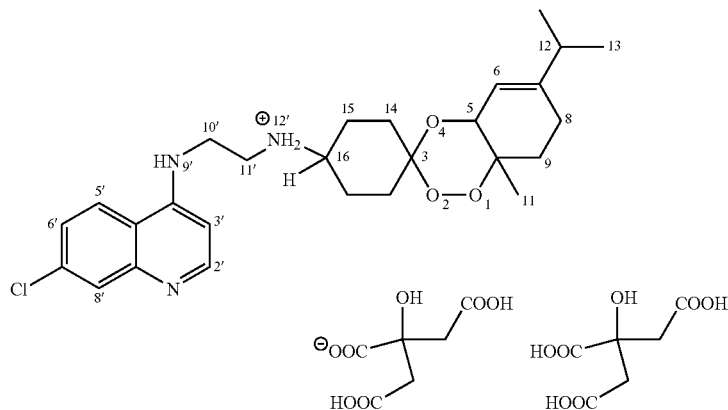
19
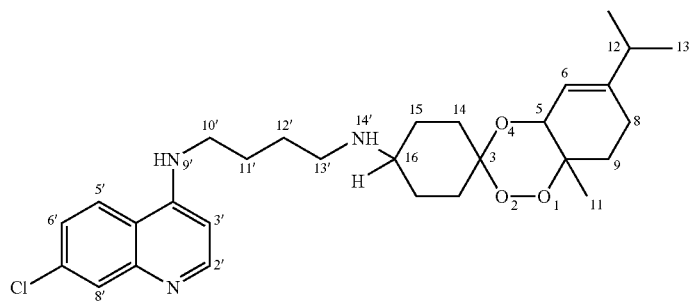
20
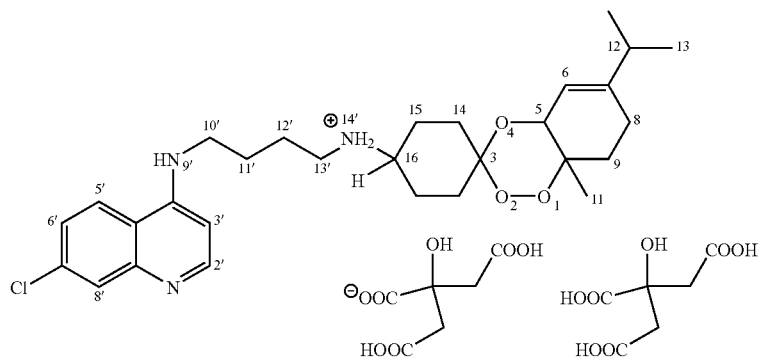
21a et 21b
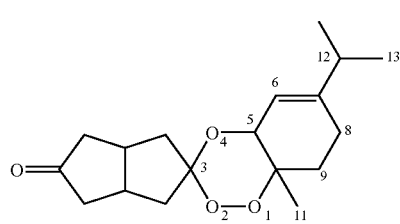

-continued
22a et 22b
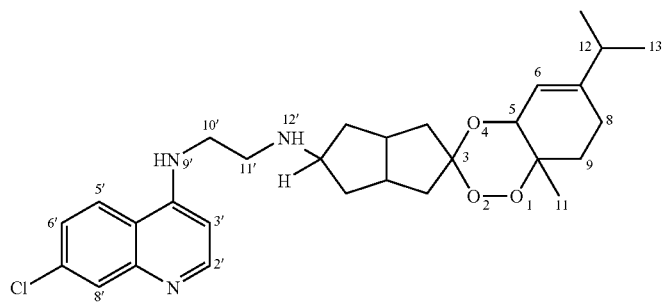
23a et 23b
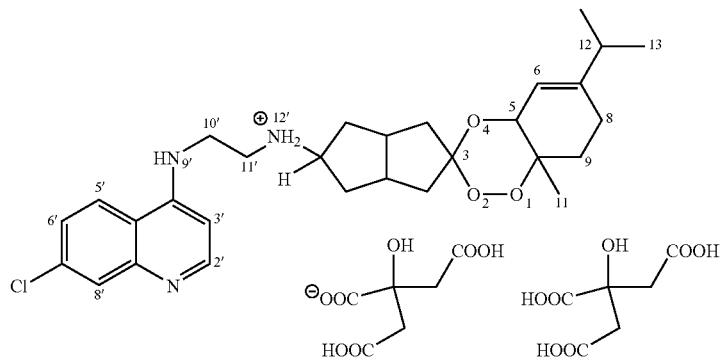
24a et 24b
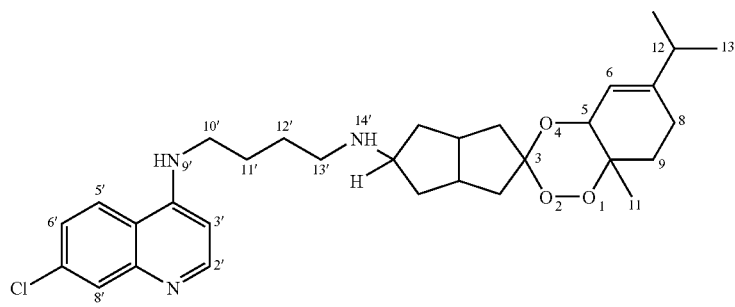
25a et 25b
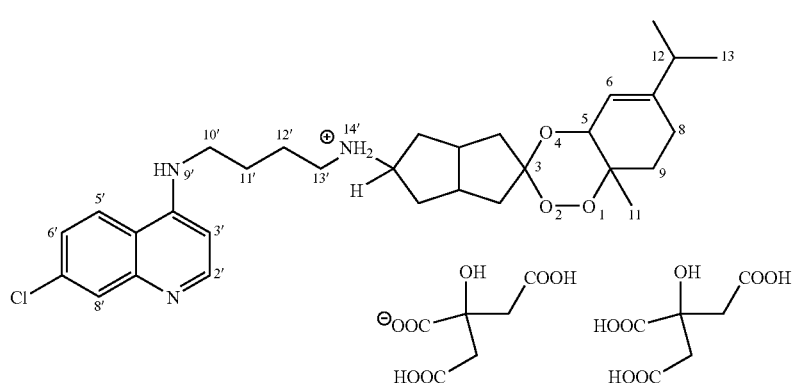
26a et 26b
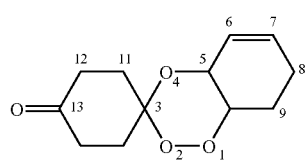
27a et 27b
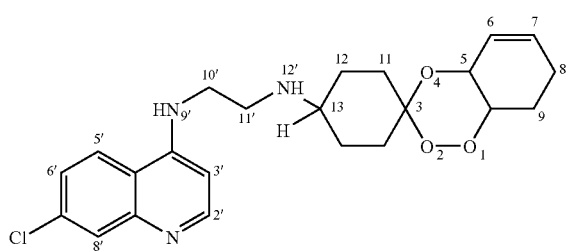

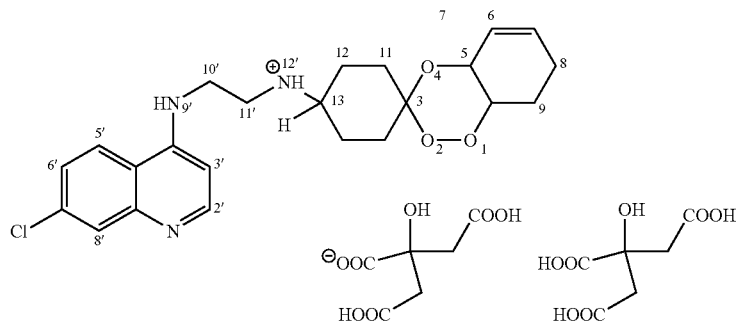
28a et 28b
29
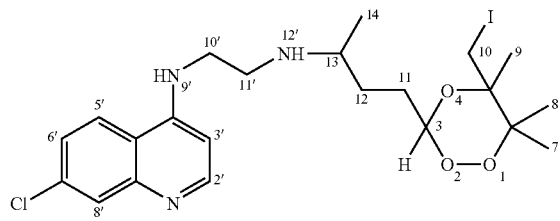
30
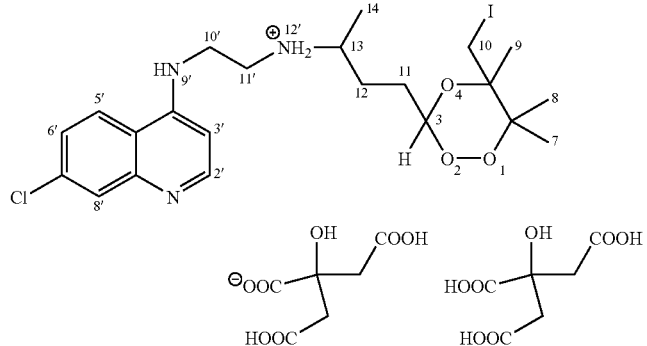
31
32
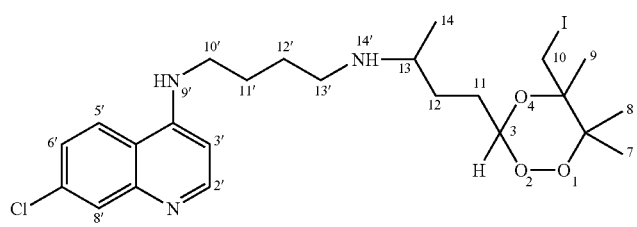
33

-continued

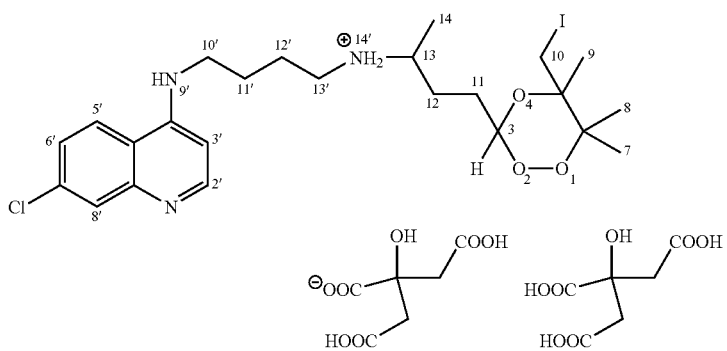

The invention claimed is:

1. A dual molecule comprising a coupling product with anti-malarial activity and having formula (I)

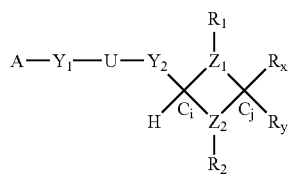

wherein

A represents a residue of a molecule with anti-malarial activity, having formula (IIa), (IIb), (III), (IV), (V), (VI), (VII), (VIII), (IX) or (X), as follows:

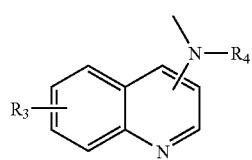

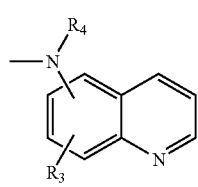

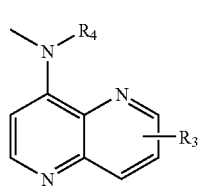

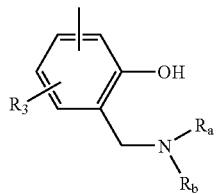

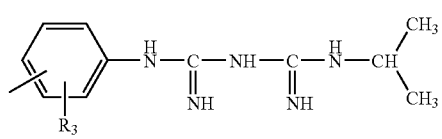

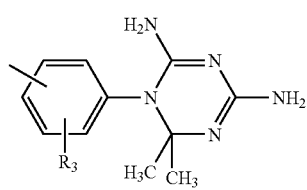

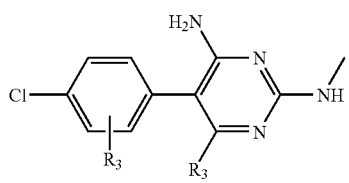

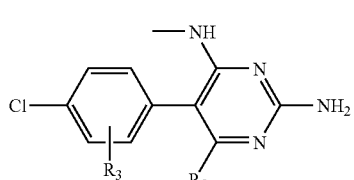

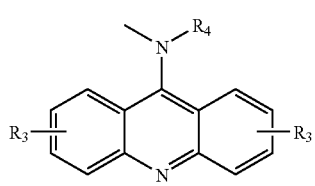

$Y_1$ and $Y_2$, identical or different, are each a linear or branched alkylene chain at C1 to C5, wherein said $Y_1$ or $Y_2$ optionally contains at least one amine, amide, sulphonamide, carboxyl, hydroxyl, ether or thioether radical, and wherein said alkylene chain at C1 to C5 is optionally substituted by an alkyl radical at C1 to C5, or either $Y_1$ or $Y_2$ is absent;

U is an amine, amide, sulfonamide, carboxyl, ether or thioether function, said function linking $Y_1$ and $Y_2$, if both $Y_1$ and $Y_2$ are present, $Z_1$ and $Z_2$, identical or different, represent a saturated or unsaturated, linear, branched or cyclic alkylene radical, including the junction carbons Ci and Cj, or either $Z_1$ or $Z_2$ is absent, or $Z_1$ and $Z_2$ together represent a cyclohexyl or bi-cyclopentyl moiety including the junction carbons Ci and Cj;

$R_1$ and $R_2$, identical or different, represent a hydrogen atom or a functional group capable of increasing the hydrosolubility of the dual molecule, said functional group selected from the group consisting of —COOH, —OH, —N($R_a$, $R_b$) wherein $R_a$ and $R_b$, identical or different, represent a hydrogen atom or alkyl radical at C1 to C5;

$R_x$ and $R_y$ form a cyclic peroxide with 4 to 8 chain links, wherein said cyclic peroxide optionally comprises 1 or 2 additional oxygen atoms in the cyclic structure, Cj being one of the peaks of said cyclic peroxide, or $R_x$ or $R_y$ is a cyclic peroxide with 4 to 8 chain links, wherein said cyclic peroxide optionally comprises 1 or 2 additional oxygen atoms in the cyclic structure, and one or more substituents $R_3$ occupying any separate positions on the cycle, wherein carbonated peaks of the cyclic peroxide are optionally substituted by one or more substituents $R_3$, wherein two adjacent substituents $R_3$ optionally form a cyclic structure with 5 to 6 chain links, saturated or unsaturated, optionally substituted by one or more substituents $R_3$ in any position, the other substituent $R_x$ or $R_y$ optionally being $R_3$;

$R_3$ represents one or more identical or different substituents occupying separate positions on the cycle, at least one substituent being a halogen atom, an —OH group, a —$CF_3$ group, an aryl radical, an alkyl or alkoxy radical at $C_1$ to $C_5$, or a —$NO_2$ group, and the other substituent or substituents being a hydrogen atom or a halogen atom, an —OH group, a —$CF_3$ group, an aryl radical, an alkyl or alkoxy radical at $C_1$ to $C_5$, or a —$NO_2$ group;

$R_4$ represents a linear, branched or cyclic alkyl radical at C1 to C5, or a hydrogen atom;

$R_5$ represents an aryl radical, a nitrous heterocyclic residue, a 9-phenanthrenyl, or a 4-quinolinyl radical, wherein $R_5$ is optionally substituted by one or more $R_3$ groups;

or an additional salt of said coupling product and a pharmacologically acceptable acid, with the proviso that said dual molecule is other than formula (I) wherein A does not represents when molecules (IIa) and (IIb) when $Y_1$ and $Y_2$, identical or different, represent a linear or branched alkylene chain at C1 to C5;

U is an amine function, said function linking $Y_1$ and $Y_2$;

$Z_1$ and $Z_2$, identical or different, represent a saturated or unsaturated, linear, branched or cyclic alkylene radical includind the junction carbons Ci and Cj, with the possibility of either $Z_1$ or $Z_2$ being absent, or $Z_1$+$Z_2$ together represent a polycyclic structure including the junction carbons Ci and Cj;

$R_1$ and $R_2$, identical or different, represent a hydrogen atom or a functional group capable of increasing the hydrosolubility of the dual molecule, advantageously selected from —COOH, —OH, —N($R_a$, $R_b$) where $R_a$ and $R_b$, identical or different, represent a hydrogen atom or alkyl radical at C1 to C5;

$R_x$ and $R_y$ form a cyclic peroxide with 4 to 8 chain links, which may comprise 1 to 2 additional oxygen atoms in the cyclic structure, Cj being one of the peaks of said cyclic peroxide;

$R_3$ represents one or more identical or different substituents occupying separate positions, at least one representing a halogen atom, an —OH group, a —$CF_3$ group, an aryl radical, an alkyl or alkoxy radical at $C_1$ to $C_5$, a —$NO_2$ group, the other substituent or substituents being a hydrogen atom or representing a halogen atom, an —OH group, a —$CF_3$ group, an aryl radical, an alkyl or alkoxy radical at $C_1$ to $C_5$, or a —$NO_2$ group;

$R_4$ represents a linear, branched or cyclic alkyl radical at C1 to C5, or a hydrogen atom;

or an addition salt of said coupling product and a pharmacologically acceptable acid.

2. A dual molecule according to claim 1 wherein $R_x$ and $R_y$ form a cyclic peroxide together.

3. A dual molecule according to claim 2 wherein $R_x$ and $R_y$ represent a trioxane substituted by one or more substituents $R_3$.

4. A dual molecule according to claim 1 wherein $R_3$ represents a single substituent, said substituent being a halogen atom selected from F, Cl, Br, I or two substituents occupying separate positions, one representing a halogen atom selected from F, Cl, Br, I, and the other an alkoxy group.

5. A dual molecule according to claim 1 wherein $Z_1$ and $Z_2$ represent a cyclohexyl or bi-cyclopentyl radical.

6. A method of preparing the dual molecule of claim 1 wherein A is an amino-quinoline and $R_x$ and $R_y$ form a trioxane, the method comprising:

(a) reacting a compound according to formula (XI)

wherein $R_3$ is as defined in claim 1 and "hal" represents a halogen atom, with a diamine derivative according to formula (XII)

wherein $R_4$ and $Y_1$ are as defined in claim 1 and $U_1$ represents an —$NH_2$ group, producing a compound according to formula (XIII)

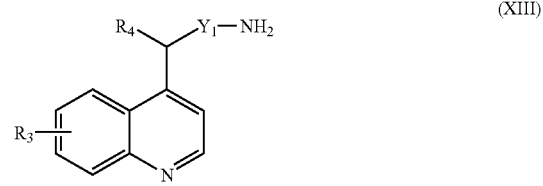

wherein $R_2$, $R_4$ and $Y_1$ are as defined in claim 1, (b) irradiating, in the presence of molecular oxygen and a photosensitizing agent, a derivative having any of formulas (XIV) to (XVII), as follow, (XIV)

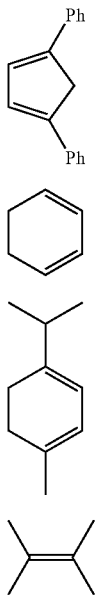

(XV)

(XVI)

(XVII)

(c) reacting the irradiated derivative with a diketone selected from the group consisting of 1,4-cyclohexadione having formula (XVIII) or cis-bicyclo(3.3.0)octane-3,7-dione having formula (XIX), (XVIII)

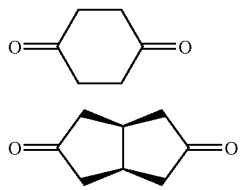

(XIX)

to produce trioxanes functionalized with a ketone, having the formula (XX)

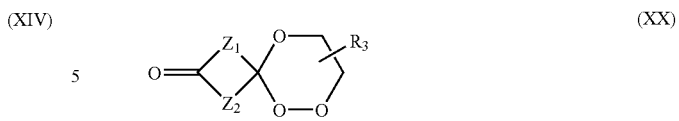

(XX)

wherein $Z_1$, $Z_2$ and $R_3$ are as defined in claim 1;

(d) coupling the derivative having formula (XIII) with the trioxane having formula (XX), by reductive amination; and (e) optionally, reacting the coupling product with a pharmaceutically acceptable acid, to provide the coupling product in salt form.

7. A pharmaceutical formulation comprising an effective quantity of at least one coupling product as defined in claim 6, associated with a pharmaceutically inert vehicle.

8. A pharmaceutical formulations according to claim 7 effective for the treatment of malaria.

9. A pharmaceutical formulation according to claim 7 in a form that is suitable for administration by the oral, rectal or injectable route.

10. A pharmaceutical formulation according to claim 9 effective for the treatment of malaria.

11. A pharmaceutical formulation according to claim 10 comprising 10 to 100 mg of active ingredient per dosage unit for oral administration.

12. A pharmaceutical formulation according to claim 11 in the form of tablets, pills, capsules or drops for oral administration.

13. A pharmaceutical formulation according to claim 11 comprising 10 to 50 mg of active ingredient per dosage unit for administration by injection.

14. A pharmaceutical formulation according to claim 9 in the form of solutions for injection by the intravenous, subcutaneous or intramuscular route, produced from sterile or sterilizable solutions, or suspensions or emulsions.

15. A method of producing a medicinal product, comprising combining a dual molecule according to claim 1 with a pharmaceutically inert vehicle to produce the medicinal product, wherein the medicinal product has an anti-malarial activity.

\* \* \* \* \*